United States Patent
Kanazawa et al.

(10) Patent No.: US 8,715,170 B2
(45) Date of Patent: May 6, 2014

(54) OBJECTIVE OPTICAL SYSTEM FOR ENDOSCOPE

(71) Applicant: Olympus Medical Systems Corp., Tokyo (JP)

(72) Inventors: Akari Kanazawa, Tokyo (JP); Tsutomu Igarashi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/723,776

(22) Filed: Dec. 21, 2012

(65) Prior Publication Data

US 2014/0018628 A1  Jan. 16, 2014

Related U.S. Application Data

(63) Continuation of application No. PCT/JP2012/065076, filed on Jun. 13, 2012.

(30) Foreign Application Priority Data

Jun. 23, 2011 (JP) ................................ 2011-139780

(51) Int. Cl.
*A61B 1/00* (2006.01)
*A61B 1/04* (2006.01)

(52) U.S. Cl.
USPC ........................................................ 600/129

(58) Field of Classification Search
CPC ............................. G02B 9/34; G02B 21/0028
USPC .................. 600/109, 129, 167–168, 172–176
See application file for complete search history.

(56) References Cited

U.S. PATENT DOCUMENTS

| | | | | |
|---|---|---|---|---|
| 2004/0240081 A1* | 12/2004 | Saito | ............................. | 359/754 |
| 2005/0046970 A1* | 3/2005 | Amanai | ........................ | 359/771 |
| 2009/0052061 A1* | 2/2009 | Asami | ........................... | 359/783 |
| 2010/0305405 A1* | 12/2010 | Miyano | ......................... | 600/168 |
| 2013/0317299 A1* | 11/2013 | Fujii | ............................. | 600/176 |

FOREIGN PATENT DOCUMENTS

| | | |
|---|---|---|
| JP | 02-293709 | 12/1990 |
| JP | 06-308381 | 11/1994 |
| JP | 11-142730 | 5/1999 |
| JP | 2000-162514 | 6/2000 |
| JP | 2002-028126 | 1/2002 |
| JP | 2004-354888 | 12/2004 |
| JP | 2005-323874 | 11/2005 |
| JP | 2009-015119 | 1/2009 |
| JP | 2009-223183 | 10/2009 |

\* cited by examiner

*Primary Examiner* — Philip R Smith
(74) *Attorney, Agent, or Firm* — Kenyon & Kenyon LLP

(57) ABSTRACT

An endoscope objective optical system includes, in order from an object side, a first lens composed of a negative single lens, a second lens composed of a positive single lens, an aperture stop, a third lens composed of a positive single lens, and a fourth lens composed of a positive combined lens, the third lens having a meniscus shape having a convex surface facing the image side. The endoscope objective optical system satisfies the following conditions:

$$0.3 < Df/f < 1.15, \quad (1)$$

$$n1 < 1.79, \quad (2)$$

$$n2 > n1, \quad (3)$$

$$0.6 < IH/f < 0.83, \quad (4)$$

and $$|r1| - |r2| + d1 > 1.8 \quad (5)$$

Df is the distance from a surface of the first lens facing the object side to the aperture stop, f is the focal length of the entire system, IH is the maximum image height of the entire system, and d1 is the center thickness of the third lens.

2 Claims, 35 Drawing Sheets

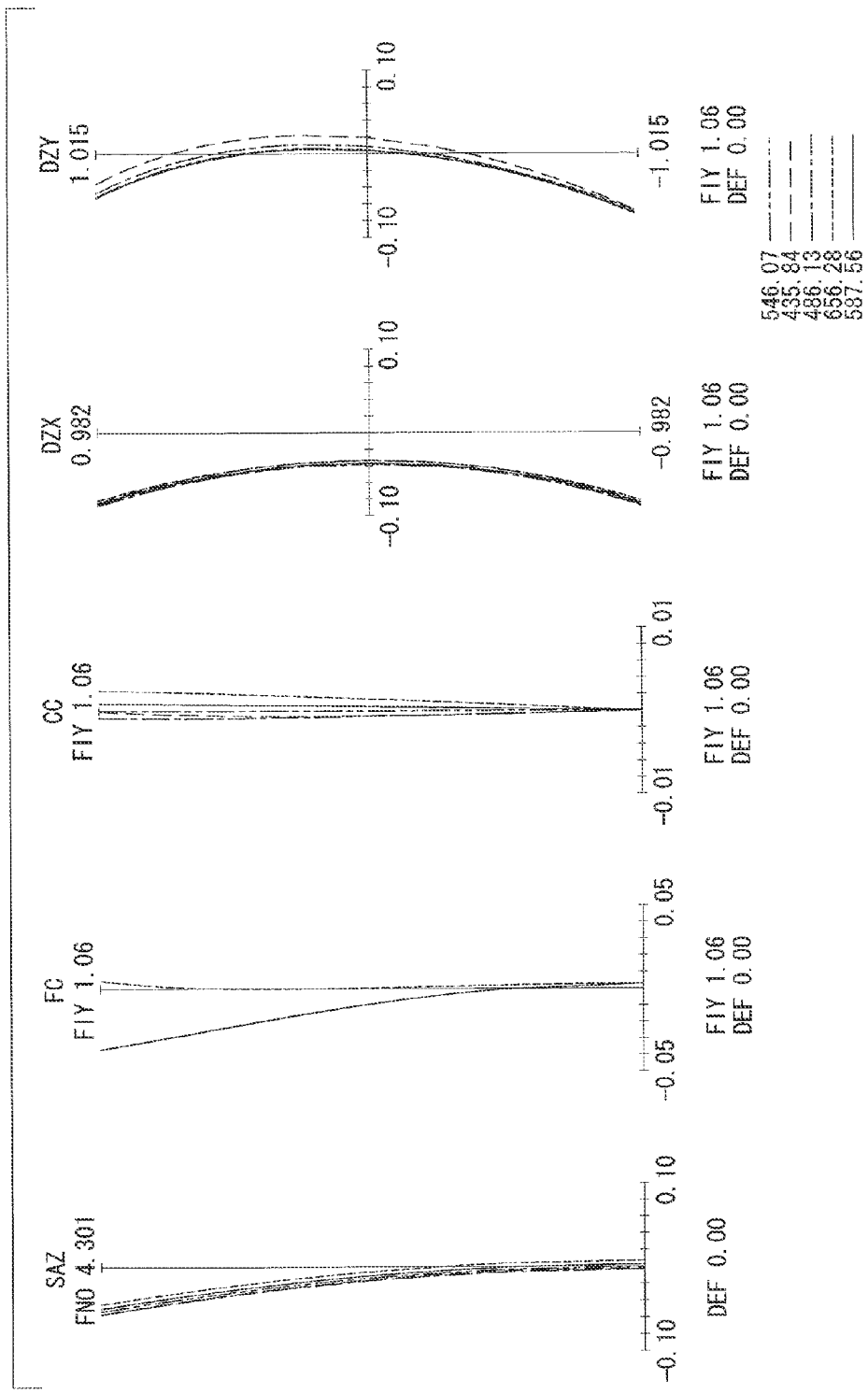

OBJECTIVE OPTICAL SYSTEM FOR ENDOSCOPE

CROSS-REFERENCE TO RELATED APPLICATIONS

This is a continuation of International Application PCT/JP2012/065076, with an international filing date of Jun. 13, 2012, which is hereby incorporated by reference herein in its entirety.

BACKGROUND OF THE INVENTION

1. Field of the Invention

The present invention relates to endoscope objective optical systems.

2. Description of Related Art

There are known wide-angle endoscope objective optical systems in the related art (see, for example, Japanese Unexamined Patent Application, Publication No. HEI-2-293709, Japanese Unexamined Patent Application, Publication No. HEI-6-308381, Japanese Unexamined Patent Application, Publication No. 2004-354888, Japanese Unexamined Patent Application, Publication No. 2009-15119, Japanese Unexamined Patent Application, Publication No. 2009-223183). Wide-angle endoscopes are extremely effective for diagnosis of the interior of the body, such as the digestive system, because there is a need for preventing a lesion from being overlooked.

These endoscope objective optical systems include, in order from the object side, a concave lens, a convex lens, a stop, a convex lens, and a combined lens, which are well-corrected for aberrations.

However, depending on the application, there is also a need for endoscopes having objective optical systems with relatively narrow angles (about 85° or less).

One such example is endoscopes for surgical use. Surgical procedures in the body require narrow-angle endoscopes.

In surgery, the surgeon performs a suitable surgical procedure while observing the procedure site in the body through an endoscope, where there is a need for magnifying the working site to facilitate the procedure. Narrow-angle endoscopes allow the surgeon to view the subject at a higher magnification than wide-angle endoscopes.

If a wide-angle endoscope is used in surgery, the endoscope needs to be brought closer to the subject for a higher magnification, which decreases the working space and therefore makes it difficult to perform a surgical procedure. In addition, the surface of the objective lens is more easily contaminated, which makes the screen less clear.

Accordingly, objective optical systems with relatively narrow angles are effective for endoscopes for surgical use. When the endoscope objective optical systems disclosed in aforementioned related art, which are well-corrected for aberrations, are applied to such narrow-angle endoscope objective optical systems without any modification, they have a problem in that they do not allow simultaneous correction for field curvature and comatic aberration.

BRIEF SUMMARY OF THE INVENTION

An aspect of the present invention provides an endoscope objective optical system including, in order from an object side, a first lens composed of a negative single lens, a second lens composed of a positive single lens, an aperture stop, a third lens composed of a positive single lens, and a fourth lens composed of a positive combined lens, wherein the third lens has a meniscus shape having a convex surface facing the image side. The endoscope objective optical system satisfies the following conditions:

$$0.3 < Df/f < 1.15 \quad (1)$$

$$n1 < 1.79 \quad (2)$$

$$n2 > n1 \quad (3)$$

$$0.6 < IH/f < 0.83 \quad (4)$$

$$|r1| - |r2| + d1 > 1.8 \quad (5)$$

wherein Df is the distance from a surface of the first lens facing the object side to the aperture stop, f is the focal length of the entire system, n1 is the refractive index of the first lens (d-line), n2 is the refractive index of the second lens (d-line), IH is the maximum image height of the entire system, r1 is the radius of curvature of a surface of the third lens facing the object side, r2 is the radius of curvature of the surface of the third lens facing the image side, and d1 is the center thickness of the third lens.

Another aspect of the present invention provides an endoscope objective optical system including, in order from an object side, a first lens composed of a negative single lens, a second lens composed of a positive single lens, an aperture stop, a third lens composed of a positive single lens, and a fourth lens composed of a positive combined lens, wherein the first lens has a flat surface facing the object side, the second lens has a flat surface facing an image side, and the third lens has a meniscus shape having a convex surface facing the image side. The endoscope objective optical system satisfies the following conditions:

$$0.3 < Df/f < 1.15 \quad (1)$$

$$n1 < 1.79 \quad (2)$$

$$n2 > n1 \quad (3)$$

$$0.6 < IH/f < 0.83 \quad (4)$$

wherein Df is the distance from a surface of the first lens facing the object side to the aperture stop, f is the focal length of the entire system, n1 is the refractive index of the first lens (d-line), n2 is the refractive index of the second lens (d-line), IH is the maximum image height of the entire system.

BRIEF DESCRIPTION OF THE SEVERAL VIEWS OF THE DRAWINGS

FIG. 35 is a set of aberration diagrams of the endoscope objective optical system having the lens arrangement in FIG. 34.

DETAILED DESCRIPTION OF THE INVENTION

An endoscope objective optical system 1 according to an embodiment of the present invention will be described below with reference to the drawings.

Figure 1:
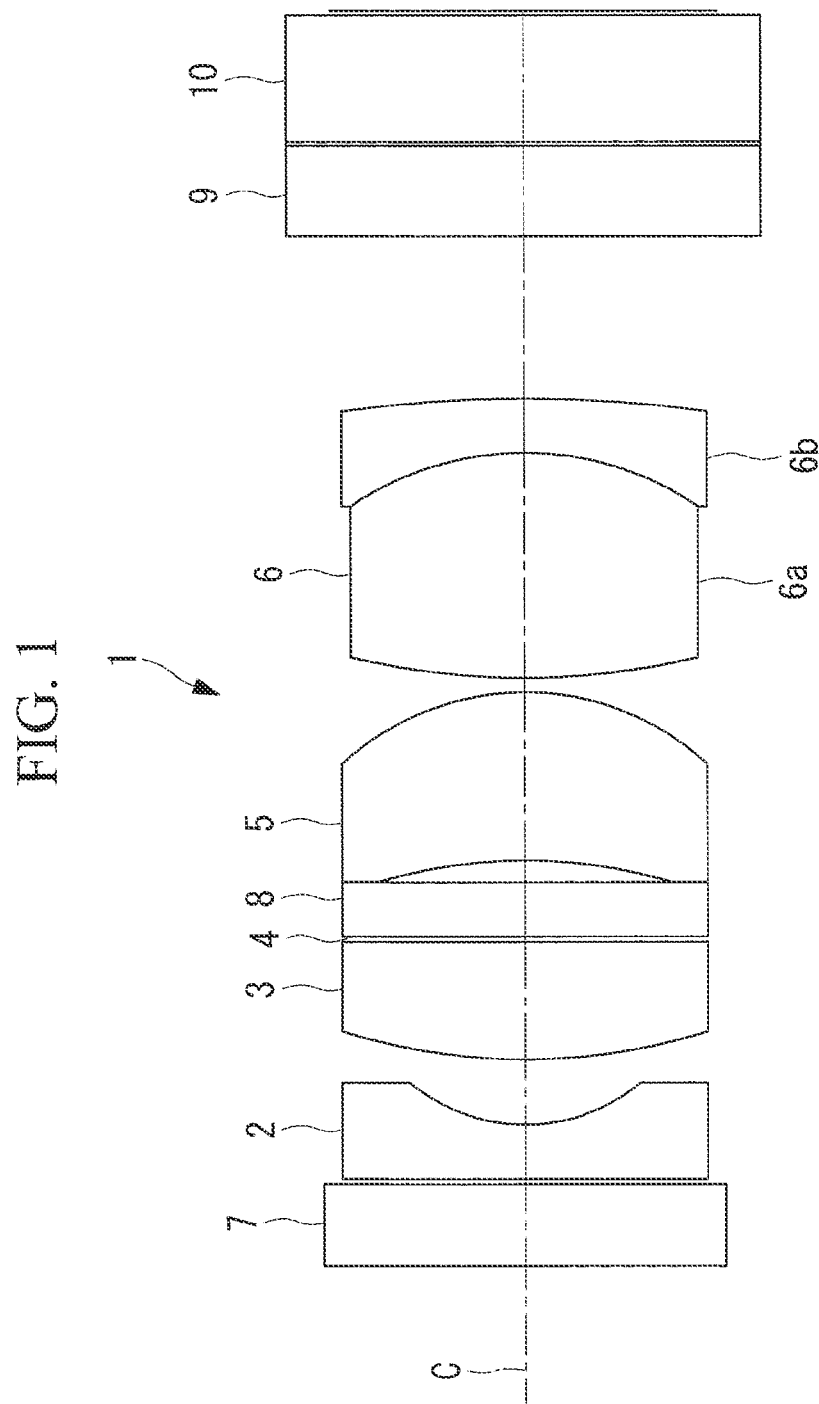
FIG. 1 is an illustration showing an endoscope objective optical system according to an embodiment of the present invention.

As shown in FIG. 1, the endoscope objective optical system 1 according to this embodiment includes, in order from the object side along an optical axis C, a first lens 2, a second lens 3, an aperture stop 4, a third lens 5, and a fourth lens 6. Reference sign 7 is a sapphire cover glass composed of a parallel flat plate. Reference sign 8 is an infrared cut filter composed of a parallel flat plate. Reference signs 9 and 10 are parallel glass plates.

The first lens 2 is composed of a plano-concave lens having a flat surface facing the object side and having negative total refractive power. The second lens 3 is composed of a plano-convex lens having a flat surface facing the image side and having positive total refractive power. The third lens 5 is composed of a meniscus lens having a convex surface facing the image side and having positive total refractive power. The fourth lens 6 is composed of a combined lens including a double-convex lens 6a and a meniscus lens 6b and having positive total refractive power.

The endoscope objective optical system 1, including the first to fourth lenses 2 to 6 and the aperture stop 4, satisfies conditions (1) to (4):

$$0.3 < Df/f < 1.15 \quad (1)$$

$$n1 < 1.79 \quad (2)$$

$$n2 > n1 \quad (3)$$

$$0.6 < IH/f < 0.83 \quad (4)$$

where Df is the distance from the surface of the first lens 2 facing the object side to the aperture stop 4, f is the focal length of the entire system 1, n1 is the refractive index of the first lens 2 (d-line), n2 is the refractive index of the second lens 3 (d-line), and IH is the maximum image height of the entire system 1.

Satisfying condition (1) decreases the ray height on the object side and thus allows for a small outer diameter. If condition (1) falls below the lower limit, the first lens 2 and the second lens 3 are difficult to fabricate. If condition (1) exceeds the upper limit, the system 1 has a wide angle, which needs to be adjusted by decreasing the power of the first lens 2 to achieve a narrow angle. If the power of the first lens 2 is decreased, however, field curvature cannot be corrected.

Satisfying condition (2) allows correction for both field curvature and comatic aberration while maintaining a short overall length.

If condition (2) exceeds the upper limit, the radius of curvature of the first lens 2 needs to be decreased to correct field curvature while maintaining a short overall length, which also results in a wide angle. Accordingly, the power of the second lens 3 needs to be increased to achieve a narrow angle. If the power of the second lens 3 is increased, however, comatic aberration cannot be corrected.

Satisfying condition (3) allows correction for field curvature while maintaining a short overall length. Satisfying condition (4) allows the objective optical system 1 to have a narrow angle.

Thus configured, the endoscope objective optical system 1 according to this exemplary embodiment provides the advantages of having a relatively narrow angle, a small outer diameter, and a short overall length and allowing simultaneous correction for field curvature and comatic aberration.

For compatibility with autoclaving, the sapphire cover glass 7 needs to be soldered to the object side of the objective optical system 1 to form a sealed structure. Because satisfying condition (1) decreases the ray height on the object side and thus allows the cover glass 7 to have a small outer diameter, a small outer diameter is also permitted for endoscope objective optical systems compatible with autoclaving. In addition, because the cover glass 7 may have a small outer diameter, stress due to soldering can be relieved, which prevents lens cracking.

For correction for field curvature, the endoscope objective optical system 1 according to this embodiment preferably satisfies condition (1'):

$$0.3 < Df/f < 0.9 \tag{1'}$$

For correction for both field curvature and comatic aberration, the endoscope objective optical system 1 according to this embodiment preferably satisfies condition (2'):

$$n1 < 1.70 \tag{2'}$$

In the endoscope objective optical system 1 according to this embodiment, the third lens 5 preferably has a meniscus shape having a convex surface facing the image side and satisfies condition (5):

$$|r1| - |r2| + d1 > 1.8 \tag{5}$$

where r1 is the radius of curvature of the surface of the third lens 5 facing the object side, r2 is the radius of curvature of the surface of the third lens 5 facing the image side, and d1 is the center thickness of the third lens 5.

If the third lens 5, which is composed of a positive single lens, has a meniscus shape having a convex surface facing the image side, such a lens is preferred for correction for both field curvature and comatic aberration.

In addition, satisfying condition (5) results in a long distance between the centers of curvature of both surfaces of the third lens 5. A long distance allows the centers of curvature to be accurately linked during a lens fabrication process, and therefore, the optical axis can be accurately determined. Thus, the third lens 5 can be accurately fabricated.

The endoscope objective optical system 1 according to this embodiment preferably satisfies condition (6):

$$-3 < f1/f < -0.9 \tag{6}$$

where f1 is the focal length of the first lens 2.

The endoscope objective optical system 1 according to this embodiment may satisfy condition (6'):

$$-3 < f1/f < -1.05 \tag{6'}$$

Satisfying condition (6) maintains a short overall length. If condition (6) falls below the lower limit, the objective optical system 1 has a long overall length. If condition (6) exceeds the upper limit, the first lens 2 is difficult to fabricate. Satisfying condition (6') facilitates fabrication of the first lens 2.

In the invention, the first lens 2 may have a flat surface facing the object side, the second lens 3 may have a flat surface facing the image side, and the third lens 5 may have a meniscus shape having a convex surface facing the image side.

This structure facilitates fabrication, thus contributing to cost reduction. In addition, because the lenses and the frames are received by flat surfaces, the lenses can be fixed to the frames without being off-center. This avoids a large deviation angle and thus avoids a phenomenon by which only the periphery of an image is blurred.

EXAMPLES

In the Examples below, r is the radius of curvature, d is the inter-surface distance, n is the refractive index, and vd is the Abbe number at the d-line. The refractive index n is the refractive index for light with a wavelength of 587.56 nm. In the drawings, reference sign rn (n=1, 2, ...) is the radius of curvature of the surface with surface number n, and reference sign do (n=1, 2, ...) is the distance between the surface with surface number n and the surface with surface number n+1.

First Example

Next, a first example of the endoscope objective optical system 1 according to this embodiment will be described.

Figure 2:
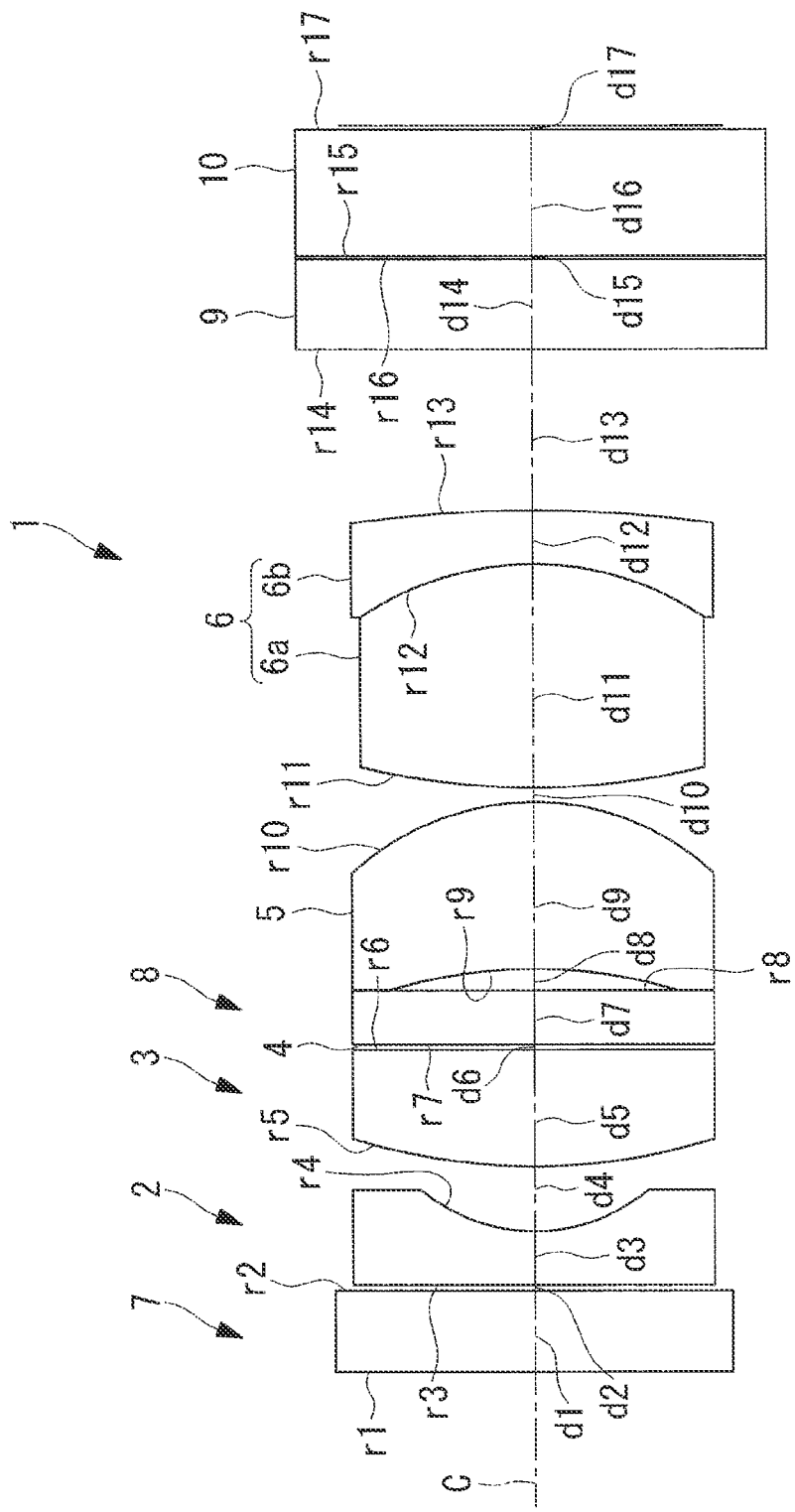
FIG. 2 is an illustration showing the lens arrangement of a first example of the endoscope objective optical system in FIG. 1.
Figure 3:
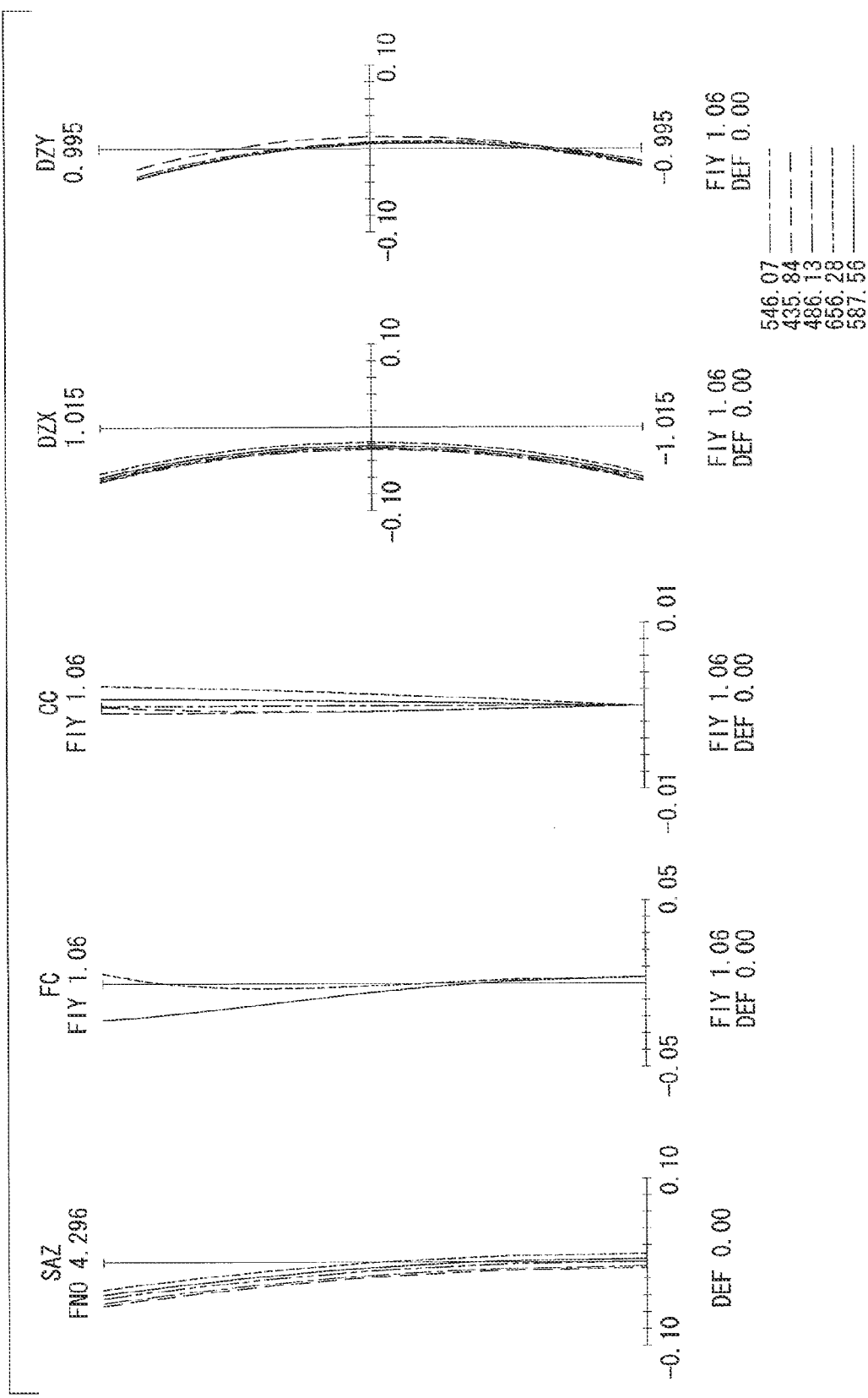
FIG. 3 is a set of aberration diagrams of the endoscope objective optical system having the lens arrangement in FIG. 2.

FIG. 2 shows the lens arrangement of the first example of the endoscope objective optical system 1. Table 1 shows lens data. FIG. 3 shows a set of aberration diagrams.

TABLE 1

| SURFACE NUMBER | r | d | n | vd |
|---|---|---|---|---|
| OBJECT SURFACE | ∞ | 36.0000 | 1. | |
| 1 | ∞ | 0.4500 | 1.76820 | 71.79 |
| 2 | ∞ | 0.0300 | 1. | |
| 3 | ∞ | 0.3000 | 1.51742 | 52.43 |
| 4 | 0.9770 | 0.3600 | 1. | |
| 5 | 3.3010 | 0.6500 | 1.88300 | 40.76 |
| 6 | ∞ | 0.0300 | 1. | |
| 7 (APERTURE STOP) | ∞ | 0.3000 | 1.52113 | 66.50 |
| 8 | ∞ | 0.1200 | 1. | |
| 9 | −2.7440 | 0.9300 | 1.88300 | 40.76 |
| 10 | −1.4620 | 0.0800 | 1. | |
| 11 | 4.0210 | 1.2400 | 1.72916 | 54.68 |
| 12 | −1.6860 | 0.3000 | 1.92286 | 18.90 |
| 13 | −7.1280 | 0.8950 | 1. | |
| 14 | ∞ | 0.5000 | 1.51633 | 64.14 |
| 15 | ∞ | 0.0200 | 1.51000 | 64.05 |
| 16 | ∞ | 0.7000 | 1.61062 | 50.49 |
| 17 | ∞ | 0.0214 | 1. | |
| IMAGE SURFACE | ∞ | | 0. | |

Second Example

Next, a second example of the endoscope objective optical system 1 according to this embodiment will be described.

Figure 4:
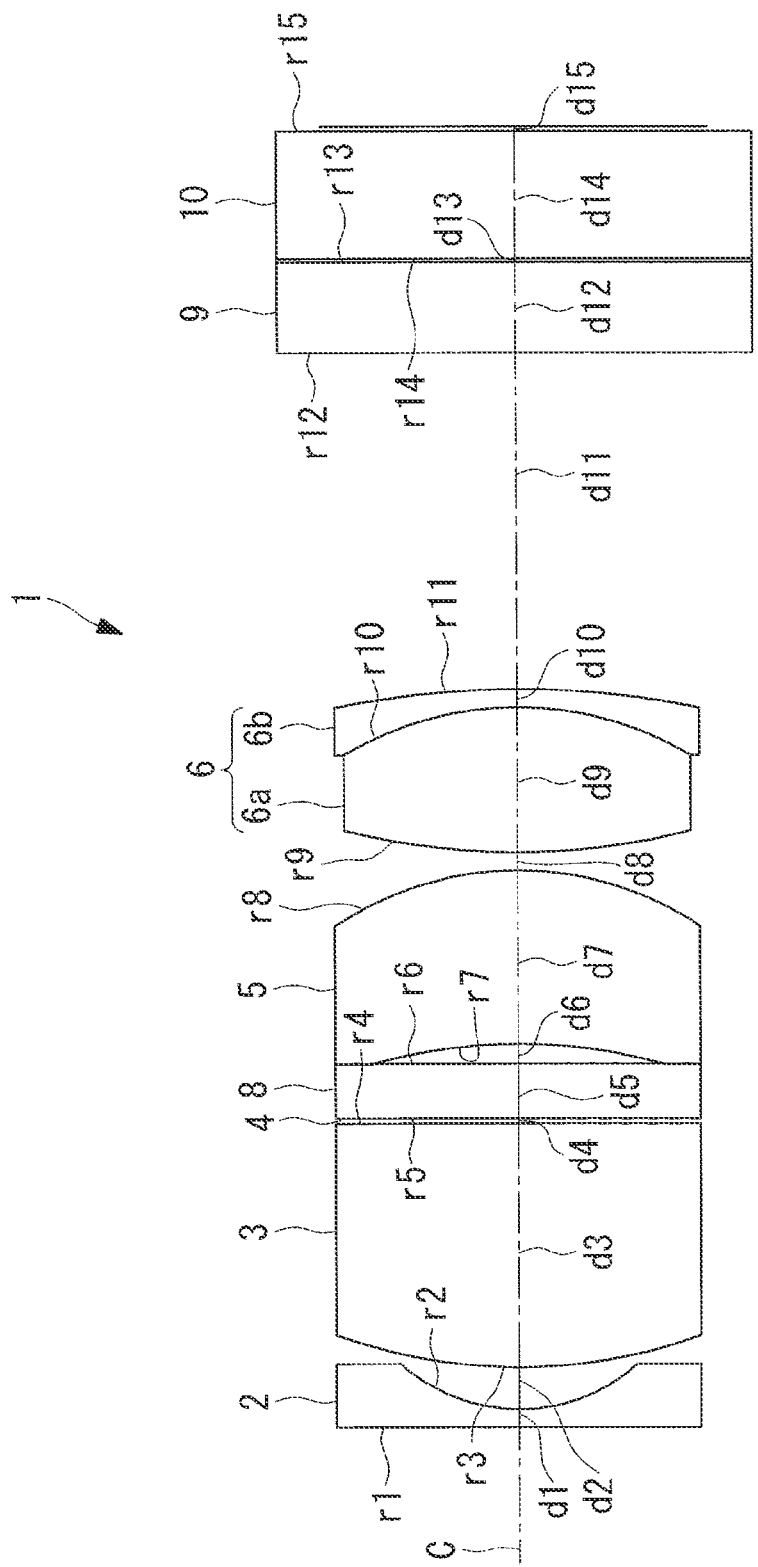
FIG. 4 is an illustration showing the lens arrangement of a second example of the endoscope objective optical system in FIG. 1.
Figure 5:
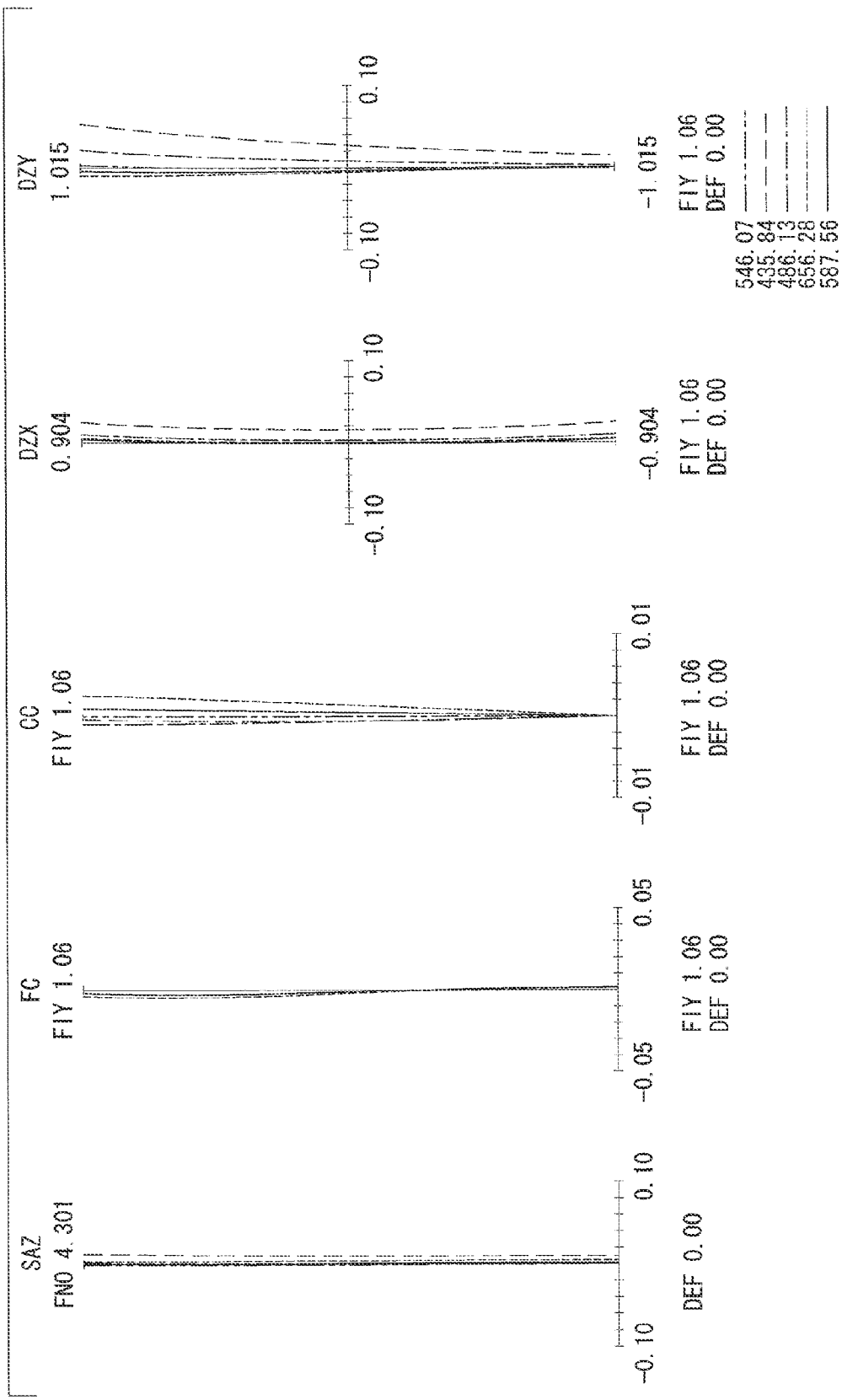
FIG. 5 is a set of aberration diagrams of the endoscope objective optical system having the lens arrangement in FIG. 4.

FIG. 4 shows the lens arrangement of the second example of the endoscope objective optical system 1. Table 2 shows lens data. FIG. 5 shows a set of aberration diagrams.

TABLE 2

| SURFACE NUMBER | r | d | n | vd |
|---|---|---|---|---|
| OBJECT SURFACE | ∞ | 33.1000 | 1. | |
| 1 | ∞ | 0.1000 | 1.69700 | 48.52 |
| 2 | 0.9724 | 0.2304 | 1. | |
| 3 | 2.8885 | 1.3477 | 1.88300 | 40.76 |
| 4 | ∞ | 0.0300 | 1. | |
| 5 (APERTURE STOP) | ∞ | 0.3000 | 1.52134 | 74.98 |
| 6 | ∞ | 0.1100 | 1. | |
| 7 | −2.9102 | 0.9600 | 1.88300 | 40.76 |
| 8 | −1.7877 | 0.1000 | 1. | |
| 9 | 3.7894 | 0.8000 | 1.72916 | 54.68 |
| 10 | −1.8454 | 0.1000 | 1.92286 | 18.90 |
| 11 | −4.9529 | 1.8557 | 1. | |
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0260 | 1. | |
| IMAGE SURFACE | ∞ | ∞ | 0. | |

Third Example

Next, a third example of the endoscope objective optical system 1 according to this embodiment will be described.

Figure 6:
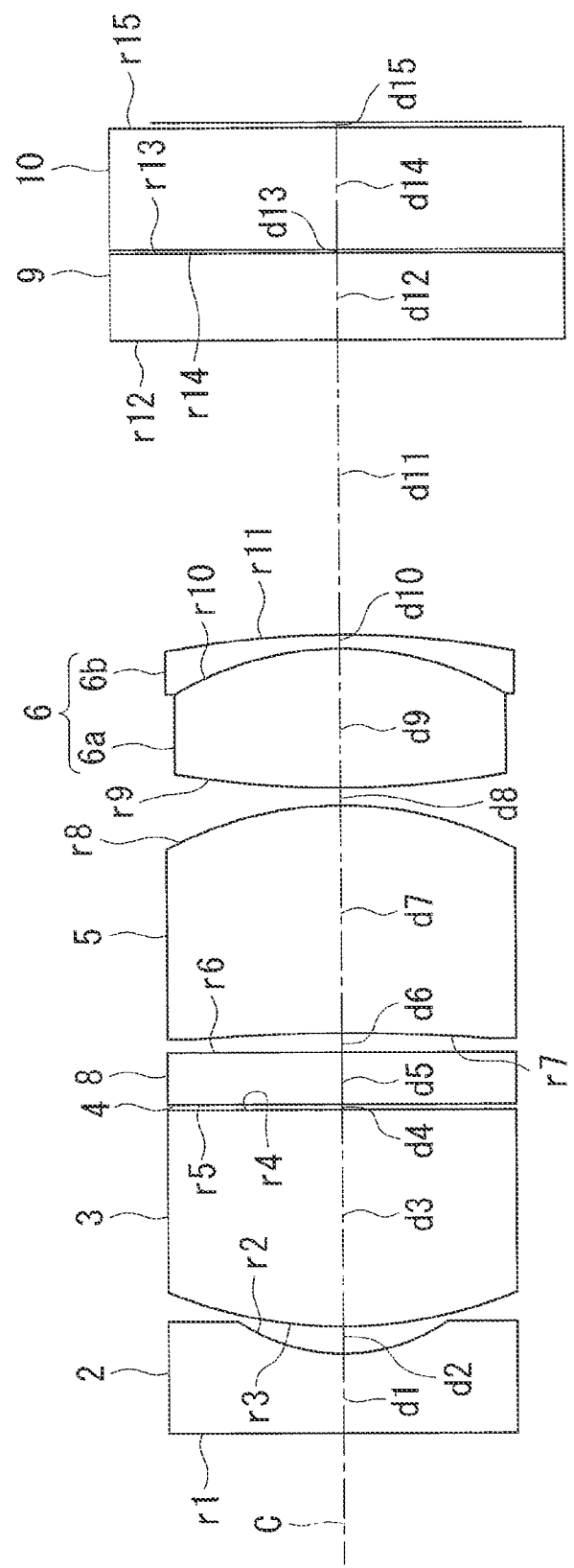
FIG. 6 is an illustration showing the lens arrangement of a third example of the endoscope objective optical system in FIG. 1.
Figure 7:
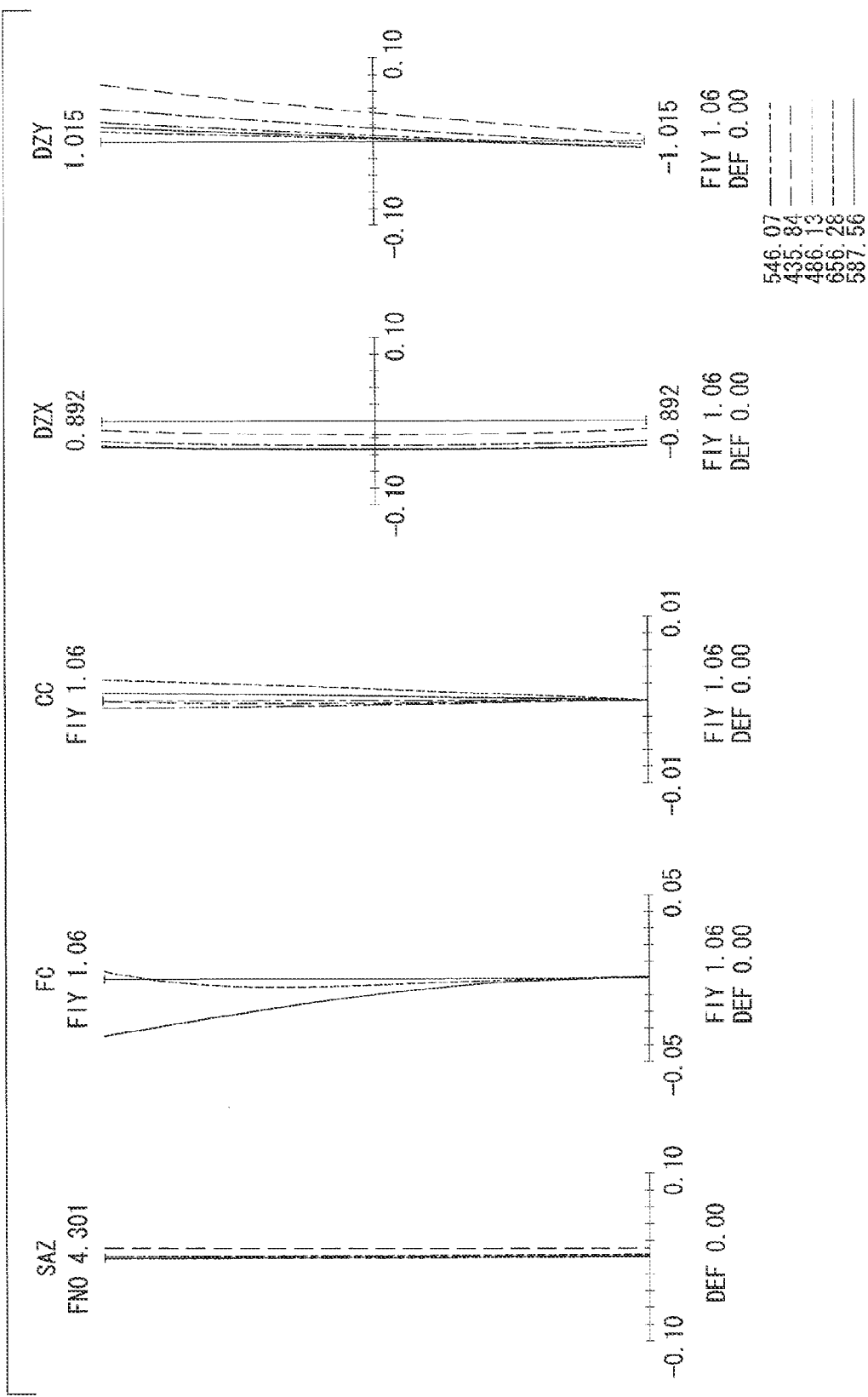
FIG. 7 is a set of aberration diagrams of the endoscope objective optical system having the lens arrangement in FIG. 6.

FIG. 6 shows the lens arrangement of the third example of the endoscope objective optical system 1. Table 3 shows lens data. FIG. 7 shows a set of aberration diagrams.

TABLE 3

| SURFACE NUMBER | r | d | n | vd |
|---|---|---|---|---|
| OBJECT SURFACE | ∞ | 33.1000 | 1. | |
| 1 | ∞ | 0.4552 | 1.69700 | 48.52 |
| 2 | 1.0564 | 0.1567 | 1. | |
| 3 | 2.6100 | 1.2495 | 1.77250 | 49.60 |
| 4 | ∞ | 0.0300 | 1. | |
| 5 (APERTURE STOP) | ∞ | 0.3000 | 1.52134 | 74.98 |
| 6 | ∞ | 0.1100 | 1. | |
| 7 | −11.3116 | 1.3143 | 1.88300 | 40.76 |
| 8 | −2.1141 | 0.1000 | 1. | |
| 9 | 5.6113 | 0.8000 | 1.72916 | 54.68 |
| 10 | −1.8594 | 0.0802 | 1.92286 | 18.90 |
| 11 | −5.4306 | 1.6955 | 1. | |
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0302 | 1. | |
| IMAGE SURFACE | ∞ | 0. | | |

Fourth Example

Next, a fourth example of the endoscope objective optical system 1 according to this embodiment will be described.

Figure 8:
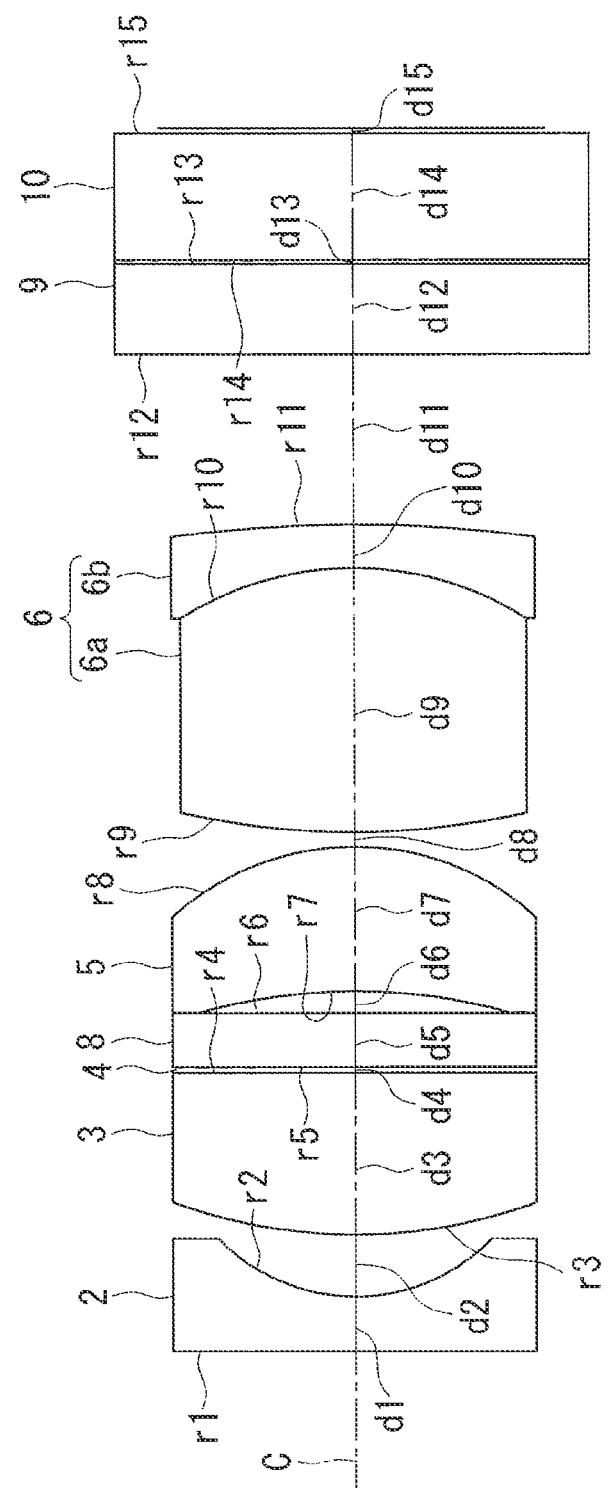
FIG. 8 is an illustration showing the lens arrangement of a fourth example of the endoscope objective optical system in FIG. 1.
Figure 9:
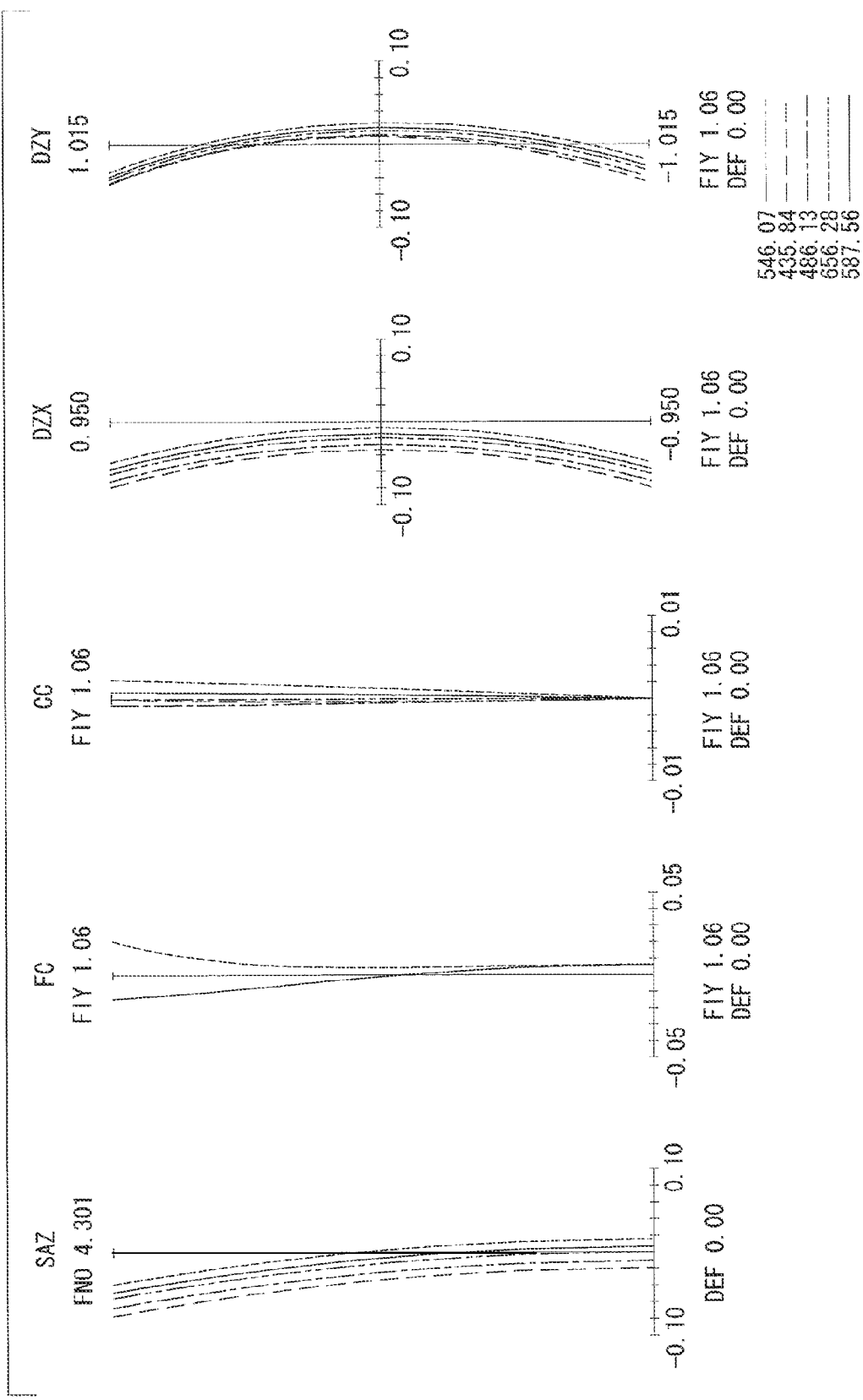
FIG. 9 is a set of aberration diagrams of the endoscope objective optical system having the lens arrangement in FIG. 8.

FIG. 8 shows the lens arrangement of the fourth example of the endoscope objective optical system 1. Table 4 shows lens data. FIG. 9 shows a set of aberration diagrams.

TABLE 4

| SURFACE NUMBER | r | d | n | vd |
|---|---|---|---|---|
| OBJECT SURFACE | ∞ | 33.1000 | 1. | |
| 1 | ∞ | 0.2999 | 1.67790 | 55.34 |
| 2 | 1.0372 | 0.3414 | 1. | |
| 3 | 2.8750 | 0.8968 | 1.88300 | 40.76 |
| 4 | ∞ | 0.0300 | 1. | |

TABLE 4-continued

| SURFACE NUMBER | r | d | n | vd |
|---|---|---|---|---|
| 5 (APERTURE STOP) | ∞ | 0.3000 | 1.52134 | 74.98 |
| 6 | ∞ | 0.1200 | 1. | |
| 7 | −3.1203 | 0.8008 | 1.88300 | 40.76 |
| 8 | −1.4689 | 0.0800 | 1. | |
| 9 | 4.3222 | 1.4557 | 1.72916 | 54.68 |
| 10 | −1.7523 | 0.2394 | 1.92286 | 18.90 |
| 11 | −7.4352 | 0.9393 | 1. | |
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0260 | 1. | |
| IMAGE SURFACE | ∞ | 0. | | |

Fifth Example

Next, a fifth example of the endoscope objective optical system 1 according to this embodiment will be described.

Figure 10:
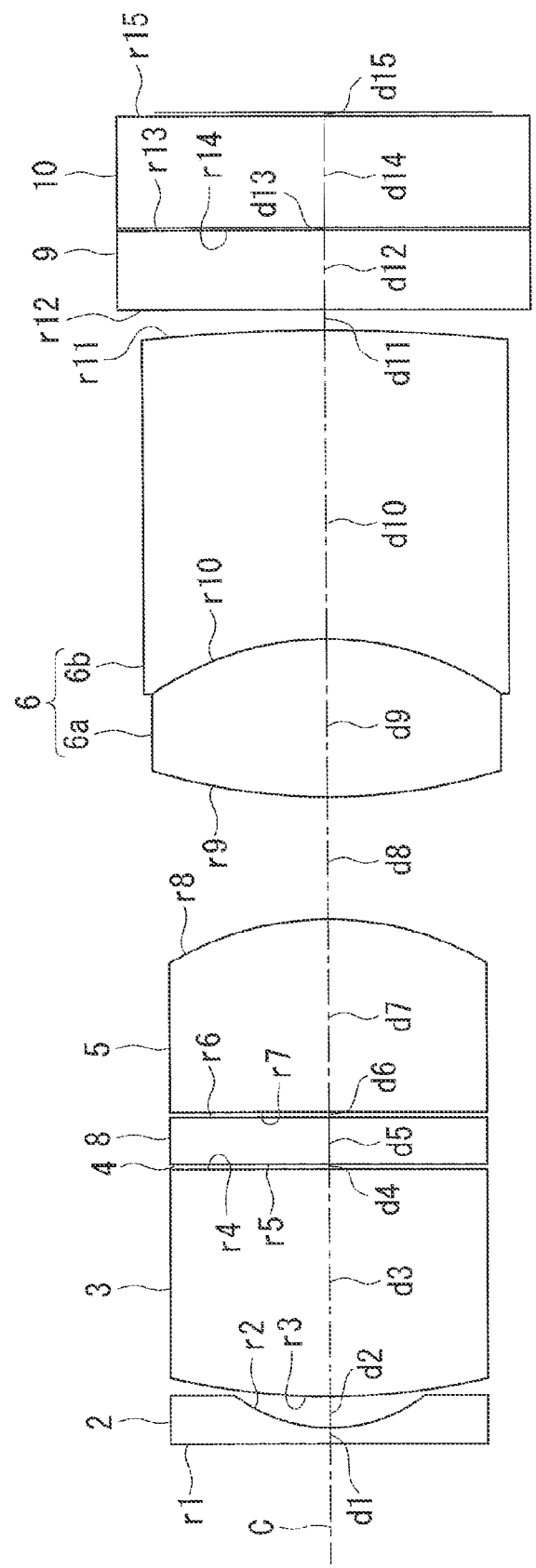
FIG. 10 is an illustration showing the lens arrangement of a fifth example of the endoscope objective optical system in FIG. 1.
Figure 11:
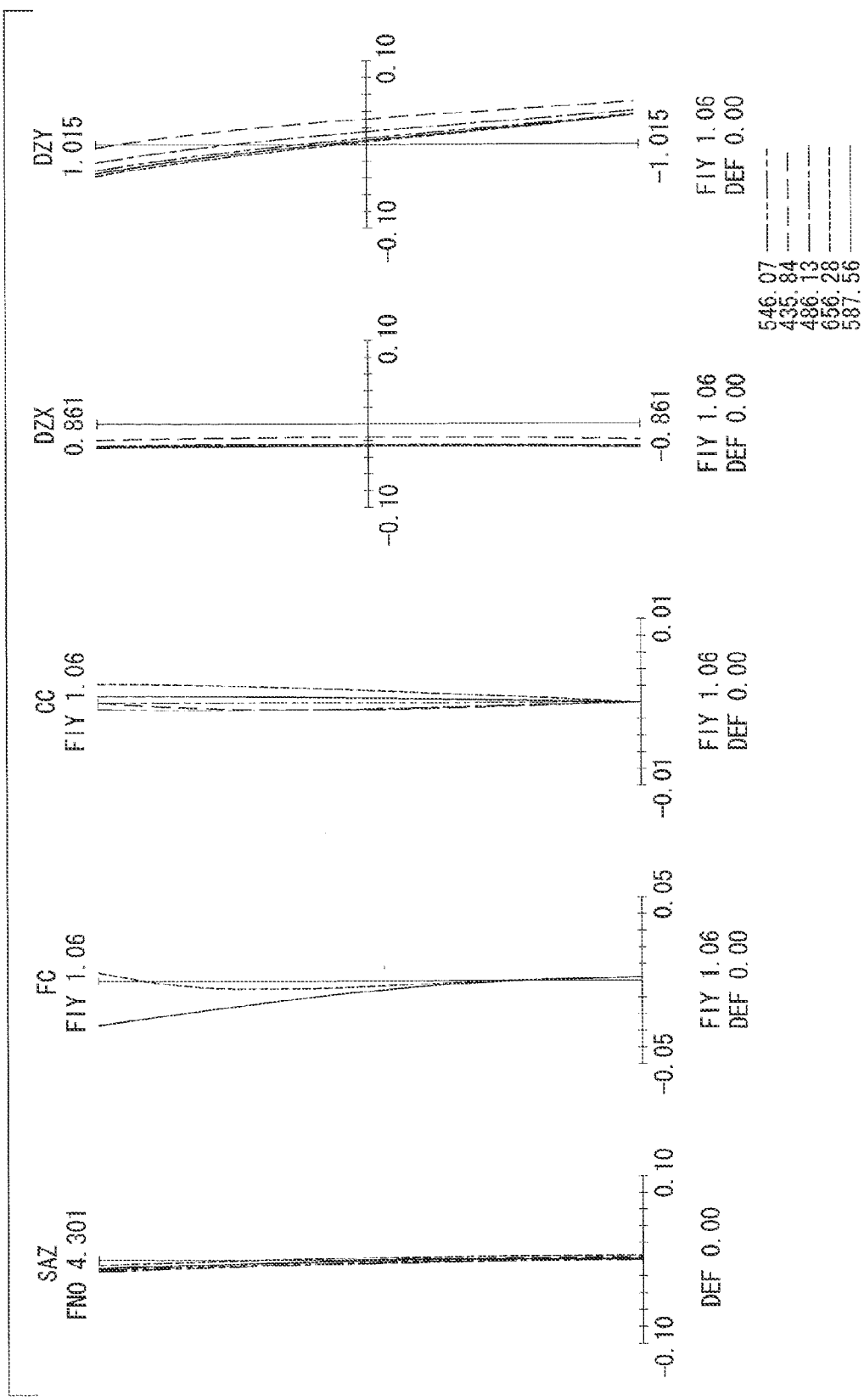
FIG. 11 is a set of aberration diagrams of the endoscope objective optical system having the lens arrangement in FIG. 10.

FIG. 10 shows the lens arrangement of the fifth example of the endoscope objective optical system 1. Table 5 shows lens data. FIG. 11 shows a set of aberration diagrams.

TABLE 5

| SURFACE NUMBER | r | d | n | vd |
|---|---|---|---|---|
| OBJECT SURFACE | ∞ | 33.1000 | 1. | |
| 1 | ∞ | 0.1000 | 1.67790 | 55.34 |
| 2 | 0.9723 | 0.1982 | 1. | |
| 3 | 4.3326 | 1.4407 | 1.88300 | 40.76 |
| 4 | ∞ | 0.0300 | 1. | |
| 5 (APERTURE STOP) | ∞ | 0.3000 | 1.52134 | 74.98 |
| 6 | ∞ | 0.0300 | 1. | |
| 7 | ∞ | 1.2264 | 1.88300 | 40.76 |
| 8 | −1.9443 | 0.7738 | 1. | |
| 9 | 3.6443 | 1.0000 | 1.72916 | 54.68 |
| 10 | −1.9195 | 1.9553 | 1.92286 | 18.90 |
| 11 | −10.9655 | 0.1300 | 1. | |
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0261 | 1. | |
| IMAGE SURFACE | ∞ | 0. | | |

Sixth Example

Next, a sixth example of the endoscope objective optical system 1 according to this embodiment will be described.

Figure 12:
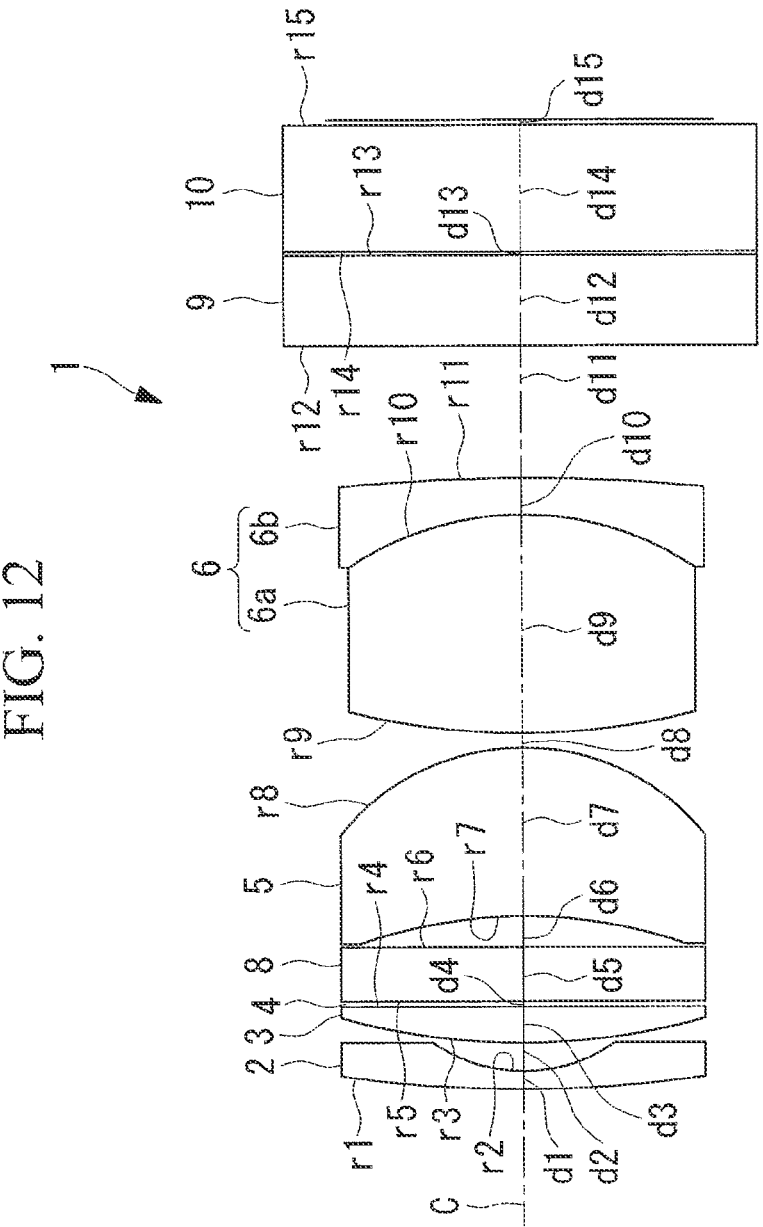
FIG. 12 is an illustration showing the lens arrangement of a sixth example of the endoscope objective optical system in FIG. 1.
Figure 13:
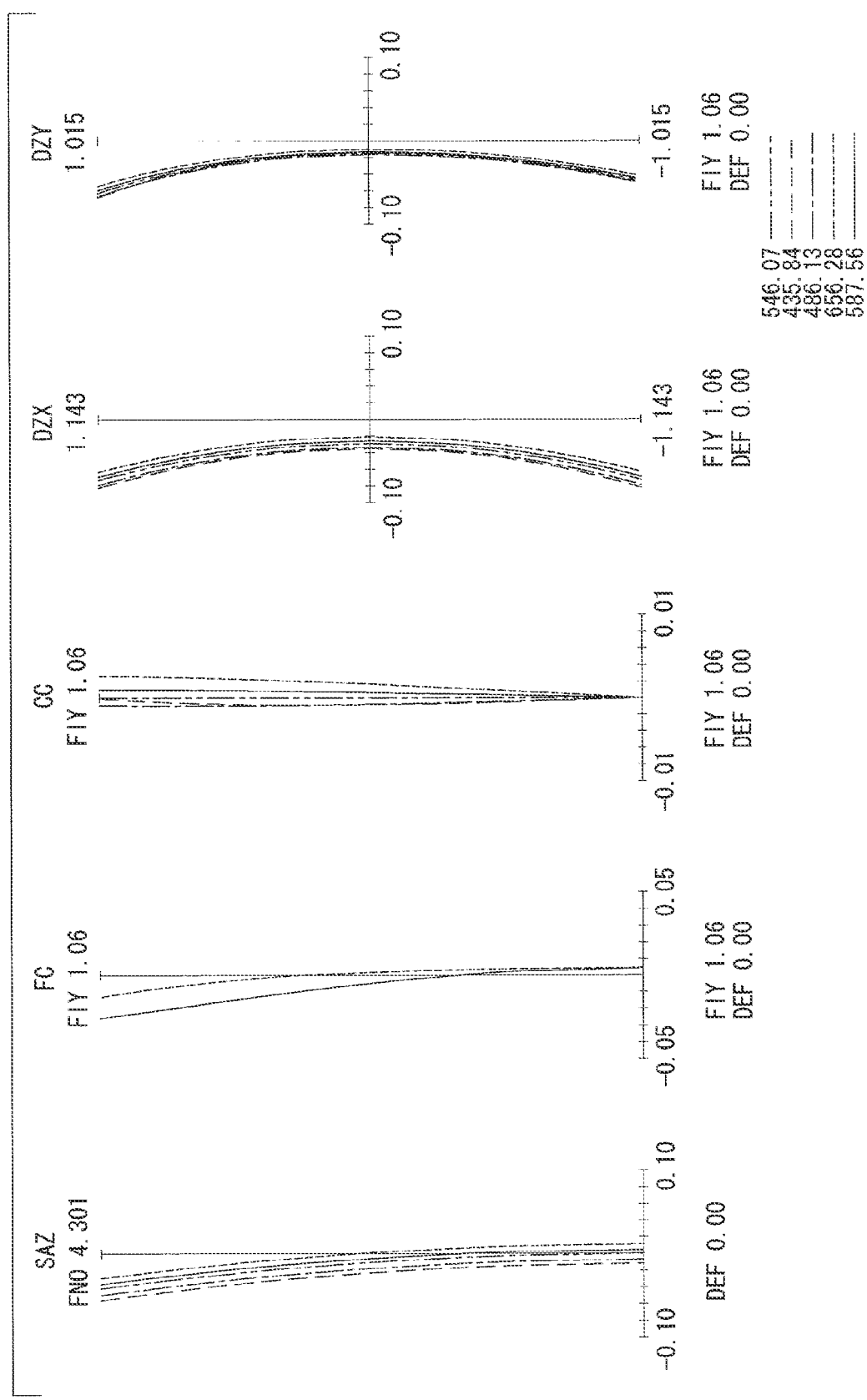
FIG. 13 is a set of aberration diagrams of the endoscope objective optical system having the lens arrangement in FIG. 12.

FIG. 12 shows the lens arrangement of the sixth example of the endoscope objective optical system 1. Table 6 shows lens data. FIG. 13 shows a set of aberration diagrams.

TABLE 6

| SURFACE NUMBER | r | d | n | vd |
|---|---|---|---|---|
| OBJECT SURFACE | ∞ | 33.1000 | 1. | |
| 1 | 6.9540 | 0.0998 | 1.51742 | 52.43 |
| 2 | 0.8630 | 0.1575 | 1. | |
| 3 | 3.7312 | 0.1979 | 1.88300 | 40.76 |
| 4 | ∞ | 0.0300 | 1. | |
| 5 (APERTURE STOP) | ∞ | 0.3000 | 1.52134 | 74.98 |
| 6 | ∞ | 0.1702 | 1. | |
| 7 | −2.7343 | 0.9348 | 1.88300 | 40.76 |
| 8 | −1.2736 | 0.0800 | 1. | |
| 9 | 3.8934 | 1.2056 | 1.72916 | 54.68 |
| 10 | −1.6906 | 0.2000 | 1.92286 | 18.90 |
| 11 | −10.5111 | 0.7297 | 1. | |
| 12 | ∞ | 0.5000 | 1.51633 | 64.14 |
| 13 | ∞ | 0.0200 | 1.51000 | 64.05 |

TABLE 6-continued

| SURFACE NUMBER | r | d | n | vd |
|---|---|---|---|---|
| 14 | ∞ | 0.7000 | 1.61062 | 50.49 |
| 15 | ∞ | 0.0261 | 1. | |
| IMAGE SURFACE | ∞ | 0. | | |

Seventh Example

Next, a seventh example of the endoscope objective optical system 1 according to this embodiment will be described.

Figure 14:
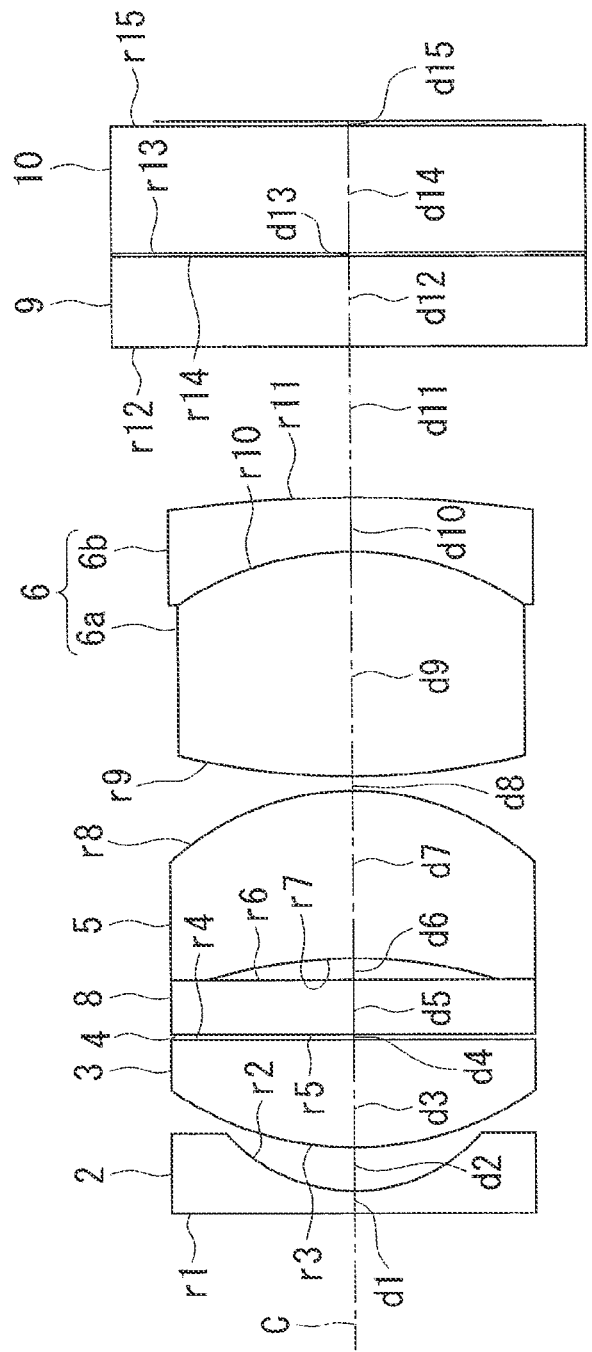
FIG. 14 is an illustration showing the lens arrangement of a seventh example of the endoscope objective optical system in FIG. 1.
Figure 15:
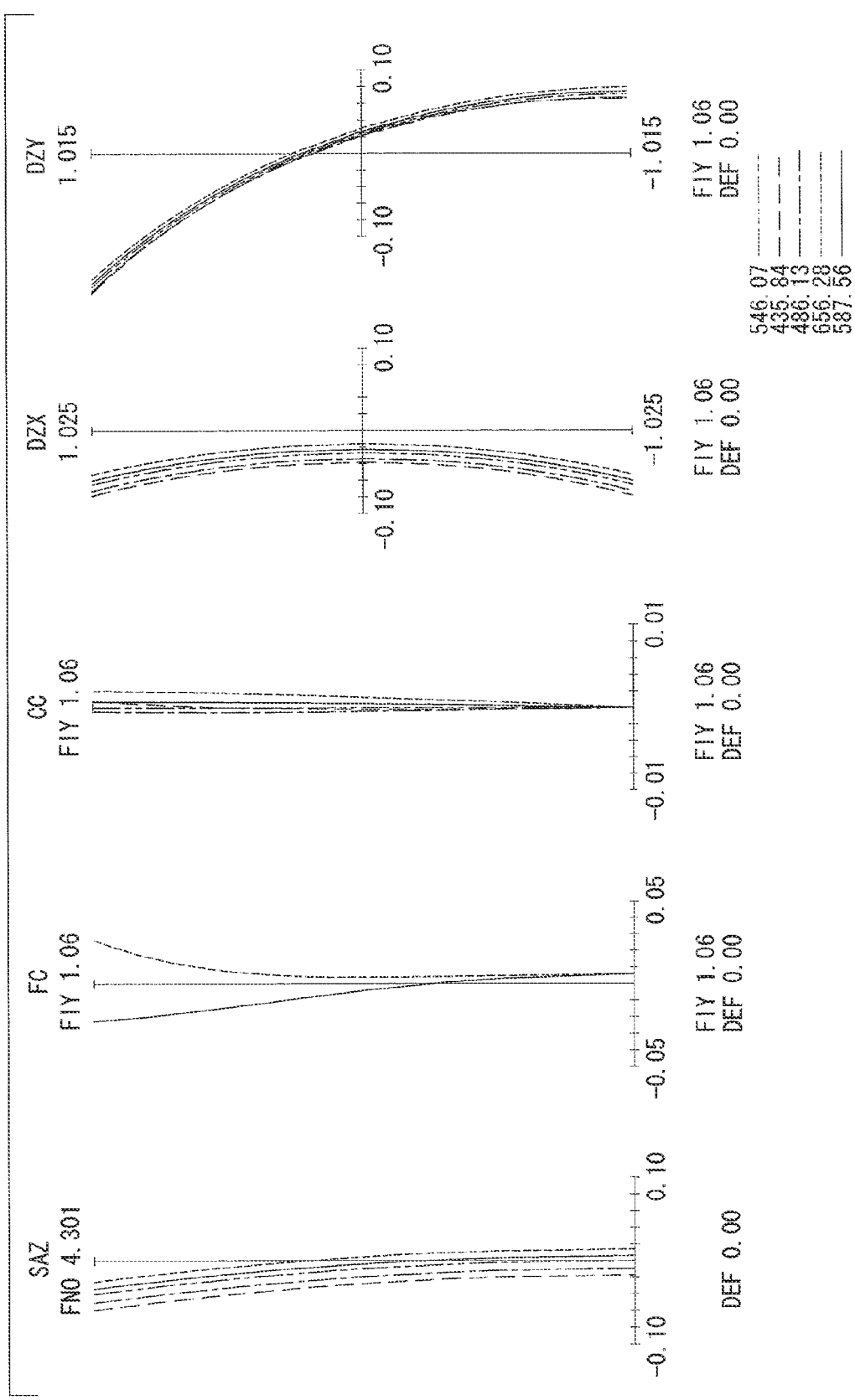
FIG. 15 is a set of aberration diagrams of the endoscope objective optical system having the lens arrangement in FIG. 14.

FIG. 14 shows the lens arrangement of the seventh example of the endoscope objective optical system 1. Table 7 shows lens data. FIG. 15 shows a set of aberration diagrams.

TABLE 7

| SURFACE NUMBER | r | d | n | vd |
|---|---|---|---|---|
| OBJECT SURFACE | ∞ | 33.1000 | 1. | |
| 1 | ∞ | 0.1241 | 1.72916 | 54.68 |
| 2 | 0.9302 | 0.2406 | 1. | |
| 3 | 1.7492 | 0.5938 | 1.88300 | 40.76 |
| 4 | ∞ | 0.0300 | 1. | |
| 5 (APERTURE STOP) | ∞ | 0.3000 | 1.52134 | 74.98 |
| 6 | ∞ | 0.1200 | 1. | |
| 7 | −2.7371 | 0.9278 | 1.88300 | 40.76 |
| 8 | −1.4620 | 0.0800 | 1. | |
| 9 | 4.0291 | 1.2400 | 1.72916 | 54.68 |
| 10 | −1.6860 | 0.3000 | 1.92286 | 18.90 |
| 11 | −7.0976 | 0.8288 | 1. | |
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0261 | 1. | |
| IMAGE SURFACE | ∞ | 0. | | |

Eighth Example

Next, an eighth example of the endoscope objective optical system 1 according to this embodiment will be described.

Figure 16:
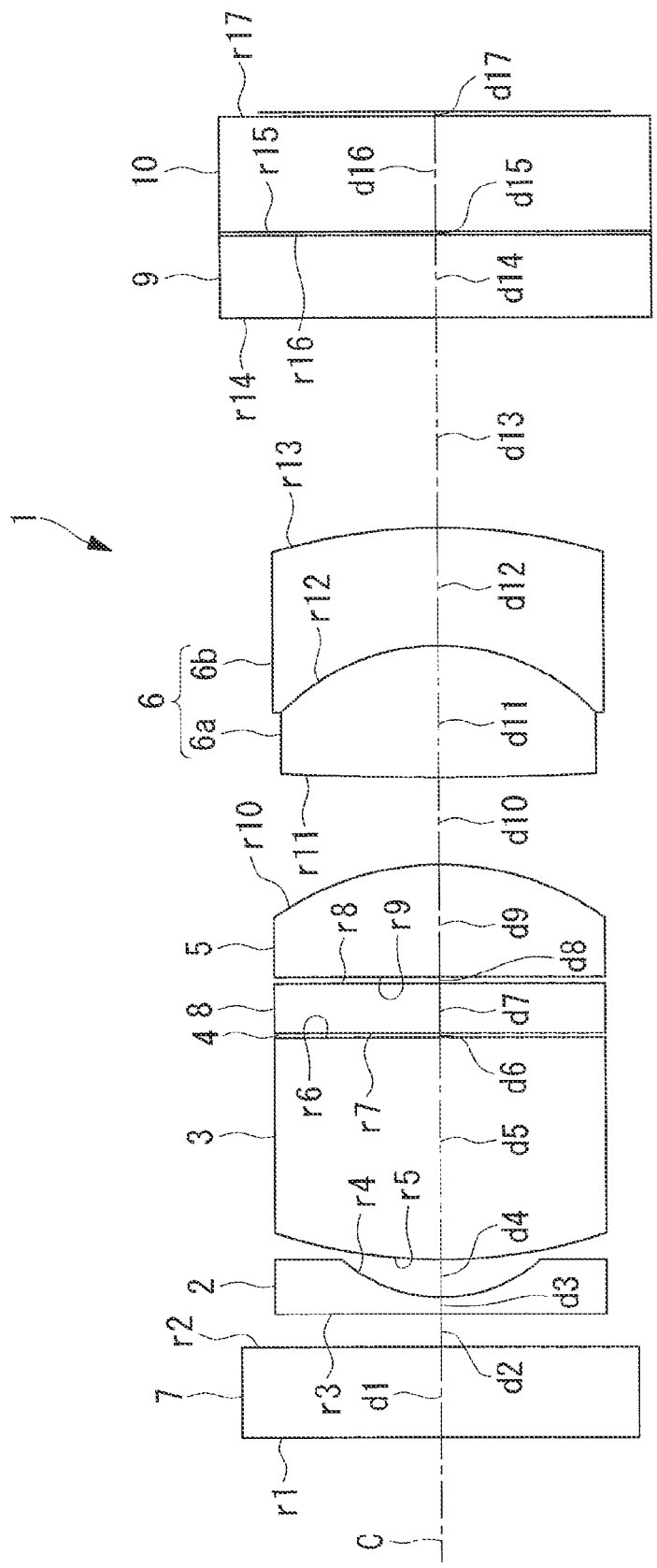
FIG. 16 is an illustration showing the lens arrangement of an eighth example of the endoscope objective optical system in FIG. 1.
Figure 17:
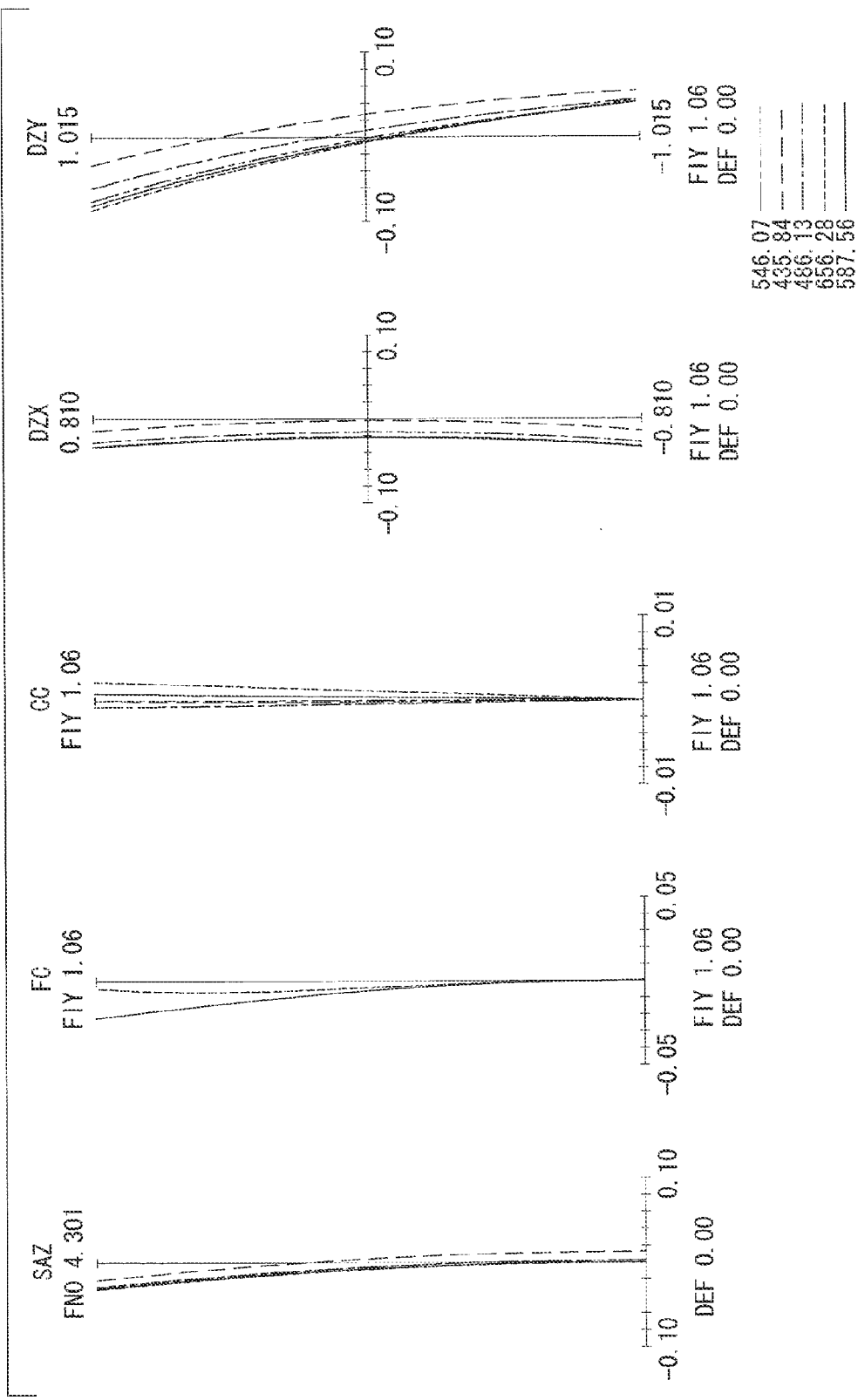
FIG. 17 is a set of aberration diagrams of the endoscope objective optical system having the lens arrangement in FIG. 16.

FIG. 16 shows the lens arrangement of the eighth example of the endoscope objective optical system 1. Table 8 shows lens data. FIG. 17 shows a set of aberration diagrams.

TABLE 8

| SURFACE NUMBER | r | d | n | vd |
|---|---|---|---|---|
| OBJECT SURFACE | ∞ | 33.1000 | 1. | |
| 1 | ∞ | 0.5500 | 1.76820 | 71.79 |
| 2 | ∞ | 0.2000 | 1. | |
| 3 | ∞ | 0.0990 | 1.78590 | 44.20 |
| 4 | 0.8977 | 0.2283 | 1. | |
| 5 | 3.1474 | 1.3514 | 1.88300 | 40.76 |
| 6 | ∞ | 0.0300 | 1. | |
| 7 (APERTURE STOP) | ∞ | 0.3000 | 1.52134 | 74.98 |
| 8 | ∞ | 0.0400 | 1. | |
| 9 | ∞ | 0.6863 | 1.88300 | 40.76 |
| 10 | −1.7031 | 0.5296 | 1. | |
| 11 | 19.3959 | 0.8000 | 1.72916 | 54.68 |
| 12 | −1.3121 | 0.7136 | 1.92286 | 18.90 |
| 13 | −3.5198 | 1.2789 | 1. | |
| 14 | ∞ | 0.5000 | 1.51633 | 64.14 |
| 15 | ∞ | 0.0200 | 1.51000 | 64.05 |
| 16 | ∞ | 0.7000 | 1.61062 | 50.49 |
| 17 | ∞ | 0.0250 | 1. | |
| IMAGE SURFACE | ∞ | 0. | | |

Ninth Example

Next, a ninth example of the endoscope objective optical system 1 according to this embodiment will be described.

Figure 18:
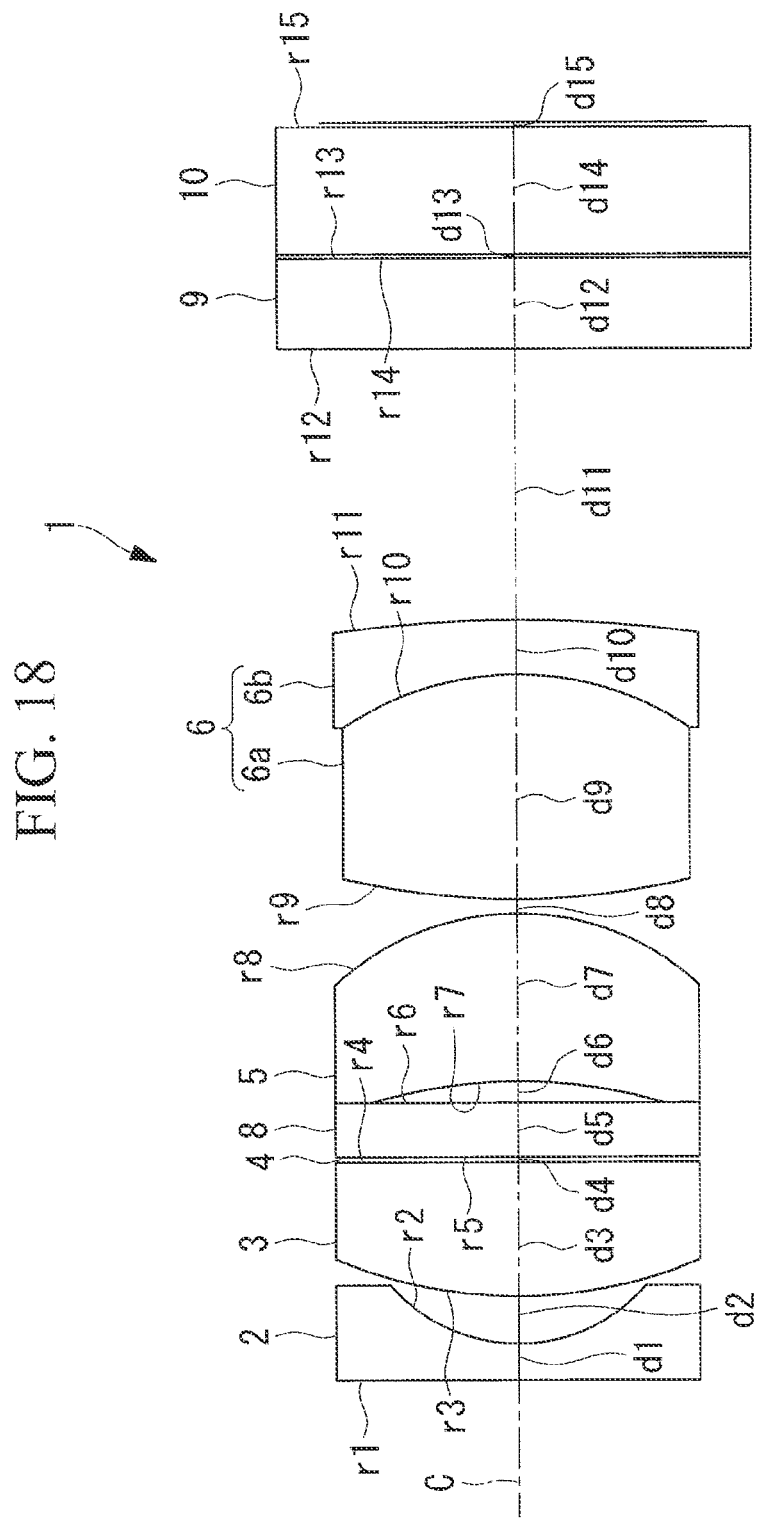
FIG. 18 is an illustration showing the lens arrangement of a ninth example of the endoscope objective optical system in FIG. 1.
Figure 19:
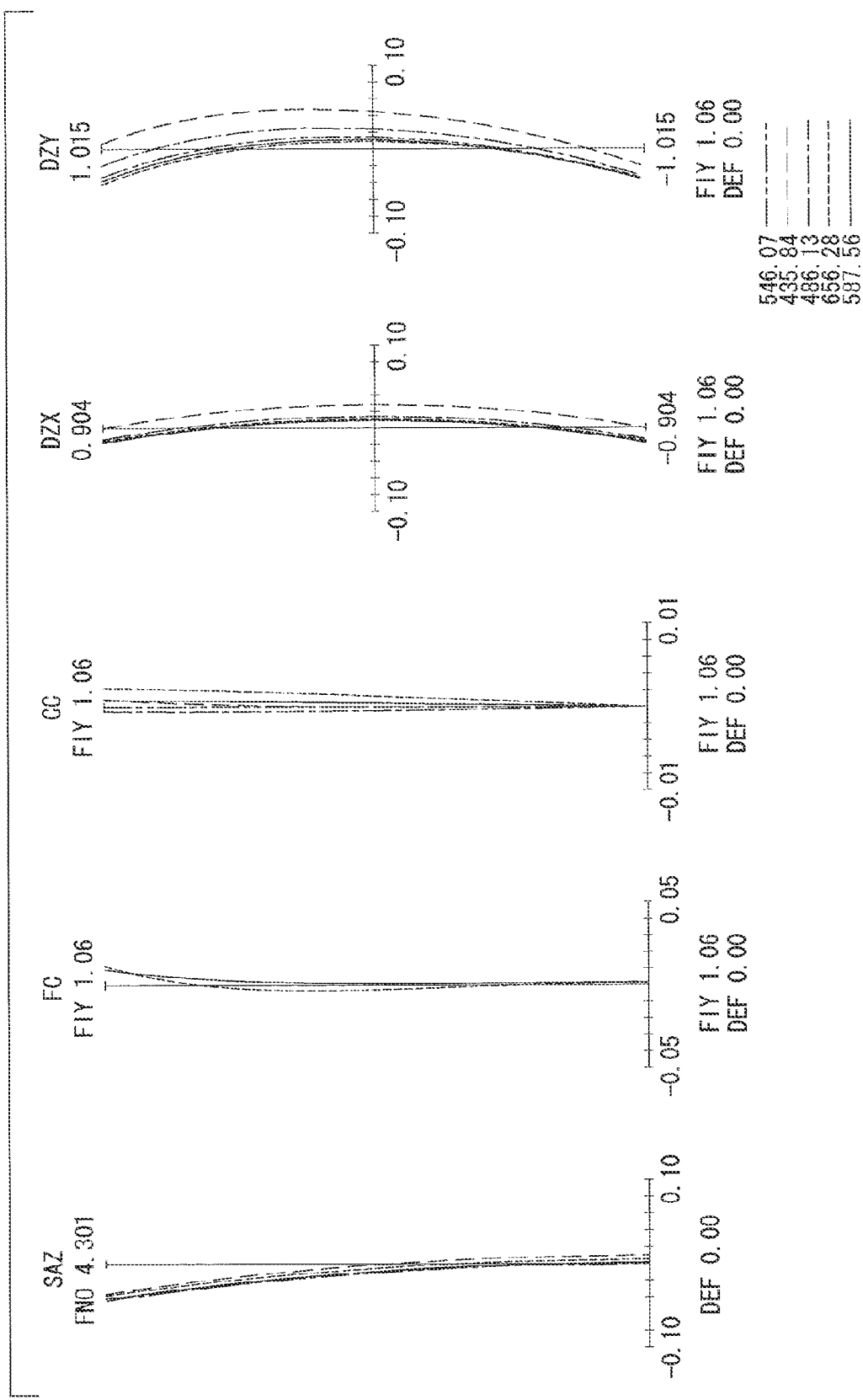
FIG. 19 is a set of aberration diagrams of the endoscope objective optical system having the lens arrangement in FIG. 18.

FIG. 18 shows the lens arrangement of the ninth example of the endoscope objective optical system 1. Table 9 shows lens data. FIG. 19 shows a set of aberration diagrams.

TABLE 9

| SURFACE NUMBER | r | d | n | vd |
|---|---|---|---|---|
| OBJECT SURFACE | ∞ | 33.1000 | 1. | |
| 1 | ∞ | 0.2000 | 1.78590 | 44.20 |
| 2 | 0.9207 | 0.2625 | 1. | |
| 3 | 2.5704 | 0.7374 | 1.88300 | 40.76 |
| 4 | ∞ | 0.0300 | 1. | |
| 5 (APERTURE STOP) | ∞ | 0.3000 | 1.52134 | 74.98 |
| 6 | ∞ | 0.1200 | 1. | |
| 7 | −2.7371 | 0.9278 | 1.88300 | 40.76 |
| 8 | −1.4620 | 0.0800 | 1. | |
| 9 | 4.0291 | 1.2400 | 1.72916 | 54.68 |
| 10 | −1.6860 | 0.3000 | 1.92286 | 18.90 |
| 11 | −7.0976 | 1.4974 | 1. | |
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0261 | 1. | |
| IMAGE SURFACE | ∞ | 0. | | |

Tenth Example

Next, a tenth example of the endoscope objective optical system 1 according to this embodiment will be described.

Figure 20:
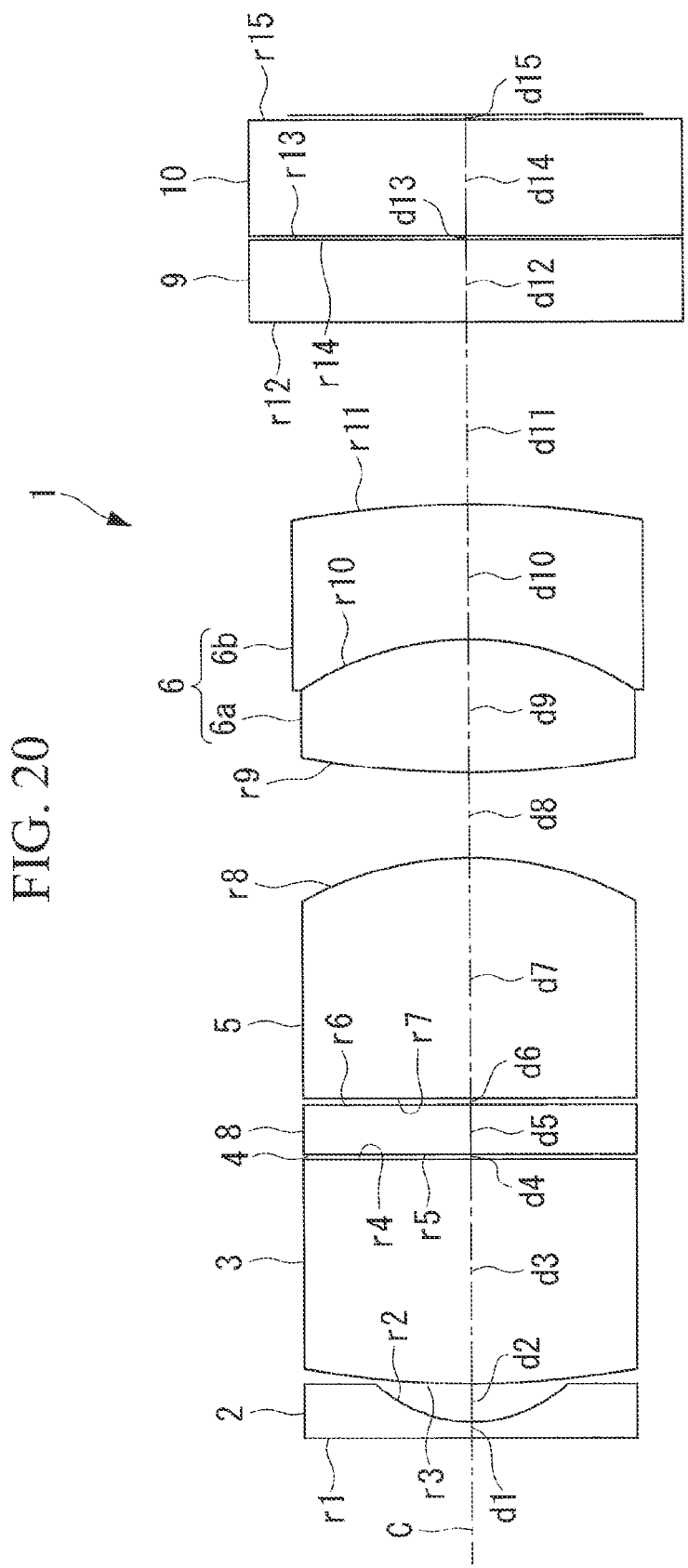
FIG. 20 is an illustration showing the lens arrangement of a tenth example of the endoscope objective optical system in FIG. 1.
Figure 21:
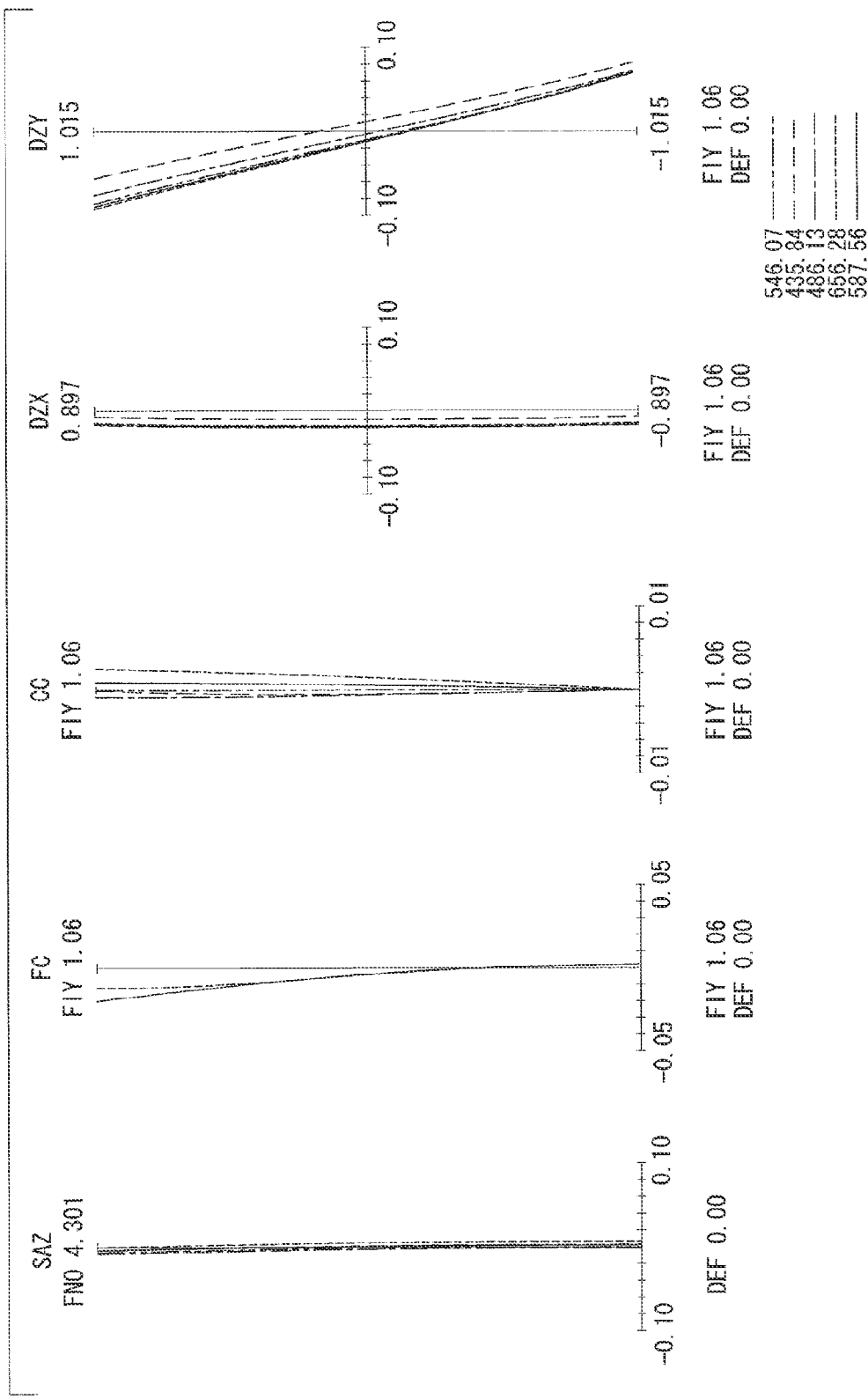
FIG. 21 is a set of aberration diagrams of the endoscope objective optical system having the lens arrangement in FIG. 20.

FIG. 20 shows the lens arrangement of the tenth example of the endoscope objective optical system 1. Table 10 shows lens data. FIG. 21 shows a set of aberration diagrams.

TABLE 10

| SURFACE NUMBER | r | d | n | vd |
|---|---|---|---|---|
| OBJECT SURFACE | ∞ | 33.1000 | 1. | |
| 1 | ∞ | 0.0987 | 1.51742 | 52.43 |
| 2 | 0.8534 | 0.2287 | 1. | |
| 3 | 5.6980 | 1.3539 | 1.88300 | 40.76 |
| 4 | ∞ | 0.0300 | 1. | |
| 5 (APERTURE STOP) | ∞ | 0.3000 | 1.52134 | 74.98 |
| 6 | ∞ | 0.0400 | 1. | |
| 7 | ∞ | 1.4573 | 1.88300 | 40.76 |
| 8 | −2.0252 | 0.5148 | 1. | |
| 9 | 5.6154 | 0.8000 | 1.72916 | 54.68 |
| 10 | −1.8041 | 0.8169 | 1.92286 | 18.90 |
| 11 | −5.7801 | 1.0995 | 1. | |
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0261 | 1. | |
| IMAGE SURFACE | ∞ | 0. | | |

Eleventh Example

Next, an eleventh example of the endoscope objective optical system 1 according to this embodiment will be described.

Figure 22:
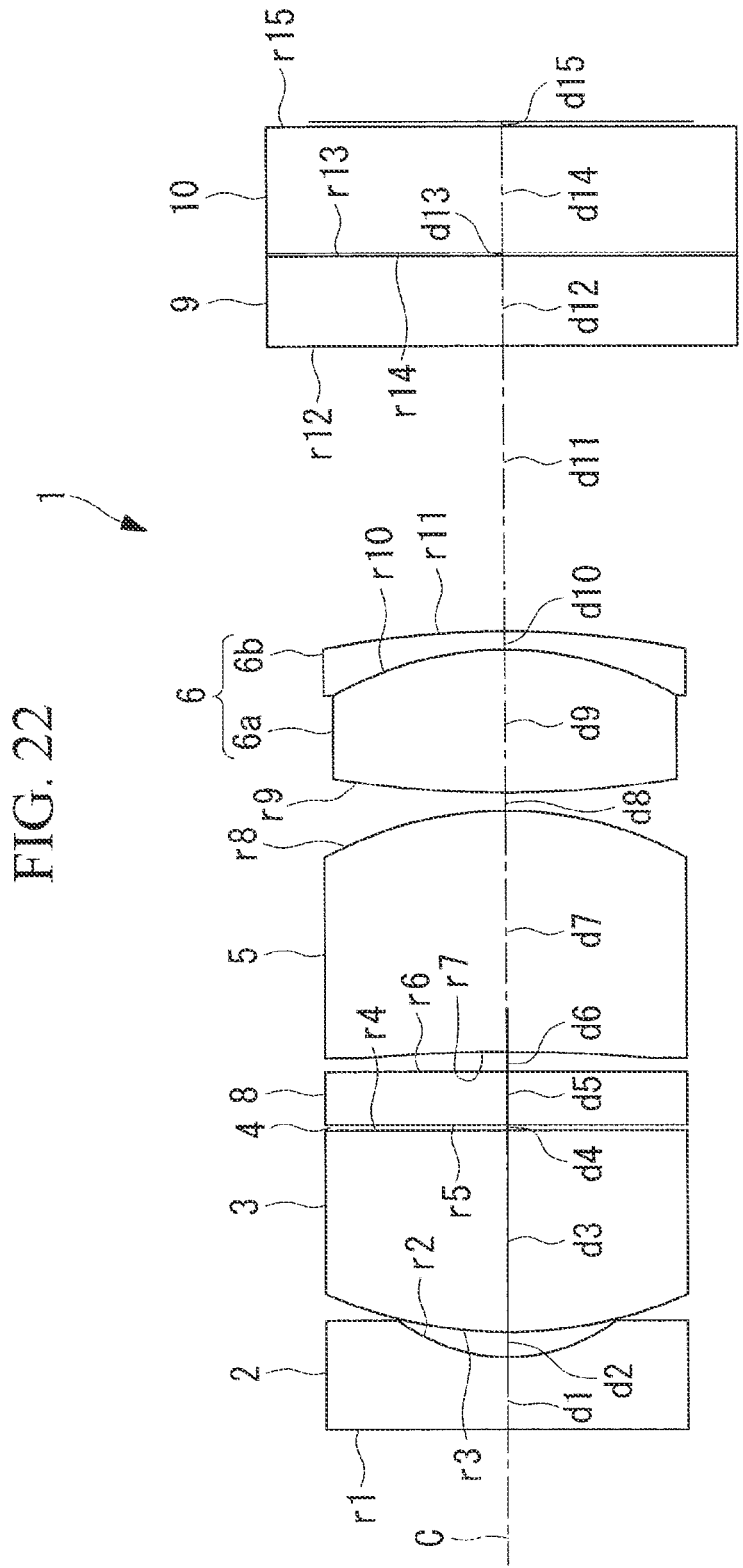
FIG. 22 is an illustration showing the lens arrangement of an eleventh example of the endoscope objective optical system in FIG. 1.
Figure 23:
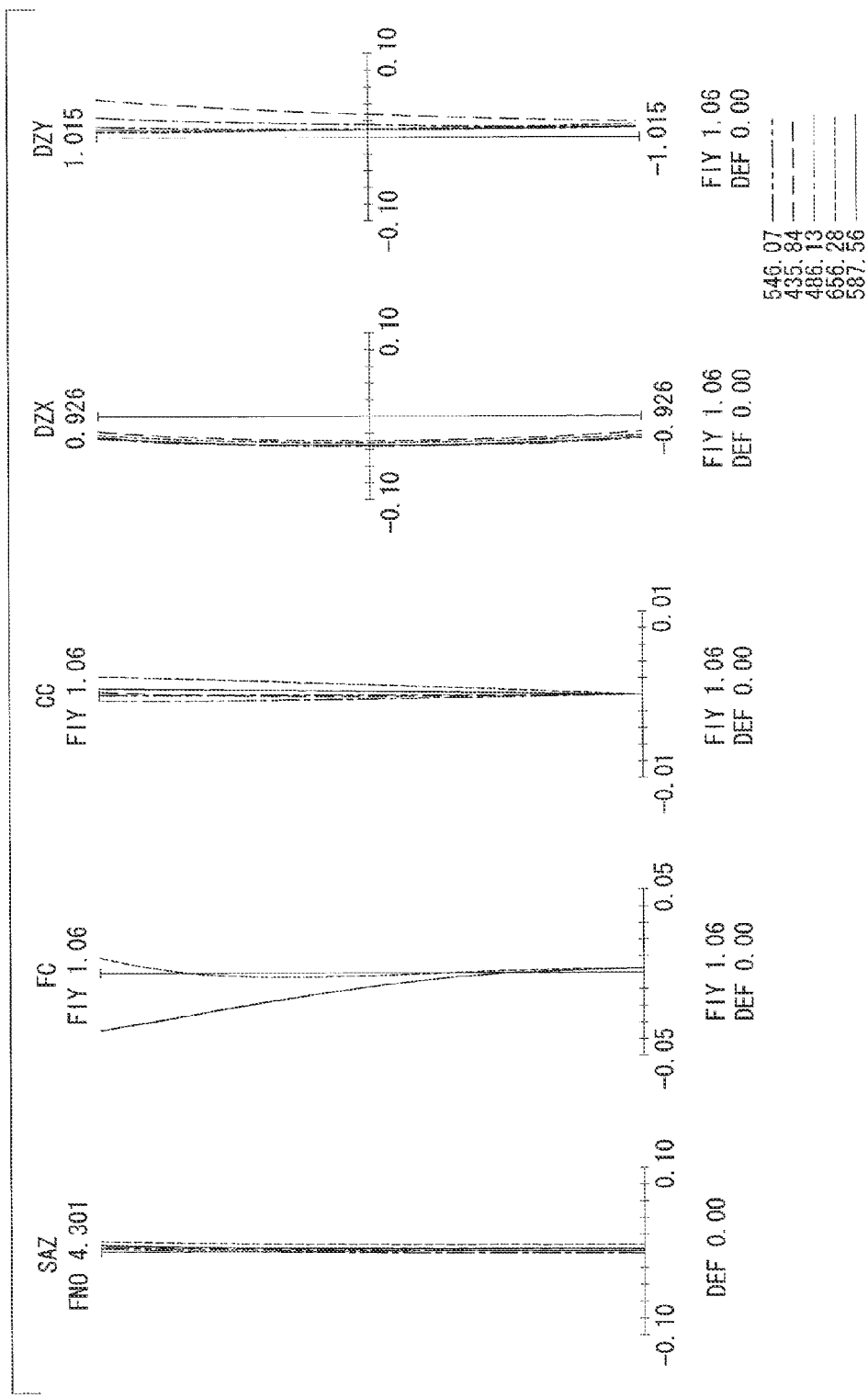
FIG. 23 is a set of aberration diagrams of the endoscope objective optical system having the lens arrangement in FIG. 22.

FIG. 22 shows the lens arrangement of the eleventh example of the endoscope objective optical system 1. Table 11 shows lens data. FIG. 23 shows a set of aberration diagrams.

TABLE 11

| SURFACE NUMBER | r | d | n | vd |
|---|---|---|---|---|
| OBJECT SURFACE | ∞ | 33.1000 | 1. | |
| 1 | ∞ | 0.4035 | 1.62280 | 57.05 |
| 2 | 0.9967 | 0.1369 | 1. | |
| 3 | 2.4904 | 1.1222 | 1.77250 | 49.60 |
| 4 | ∞ | 0.0300 | 1. | |
| 5 (APERTURE STOP) | ∞ | 0.3000 | 1.52134 | 74.98 |
| 6 | ∞ | 0.1100 | 1. | |
| 7 | −9.0139 | 1.3413 | 1.88300 | 40.76 |
| 8 | −2.0728 | 0.1000 | 1. | |
| 9 | 5.6006 | 0.8000 | 1.72916 | 54.68 |
| 10 | −1.8931 | 0.1027 | 1.92286 | 18.90 |
| 11 | −5.2543 | 1.5845 | 1. | |
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0264 | 1. | |
| IMAGE SURFACE | ∞ | 0. | | |

Twelfth Example

Next, a twelfth example of the endoscope objective optical system 1 according to this embodiment will be described.

Figure 24:
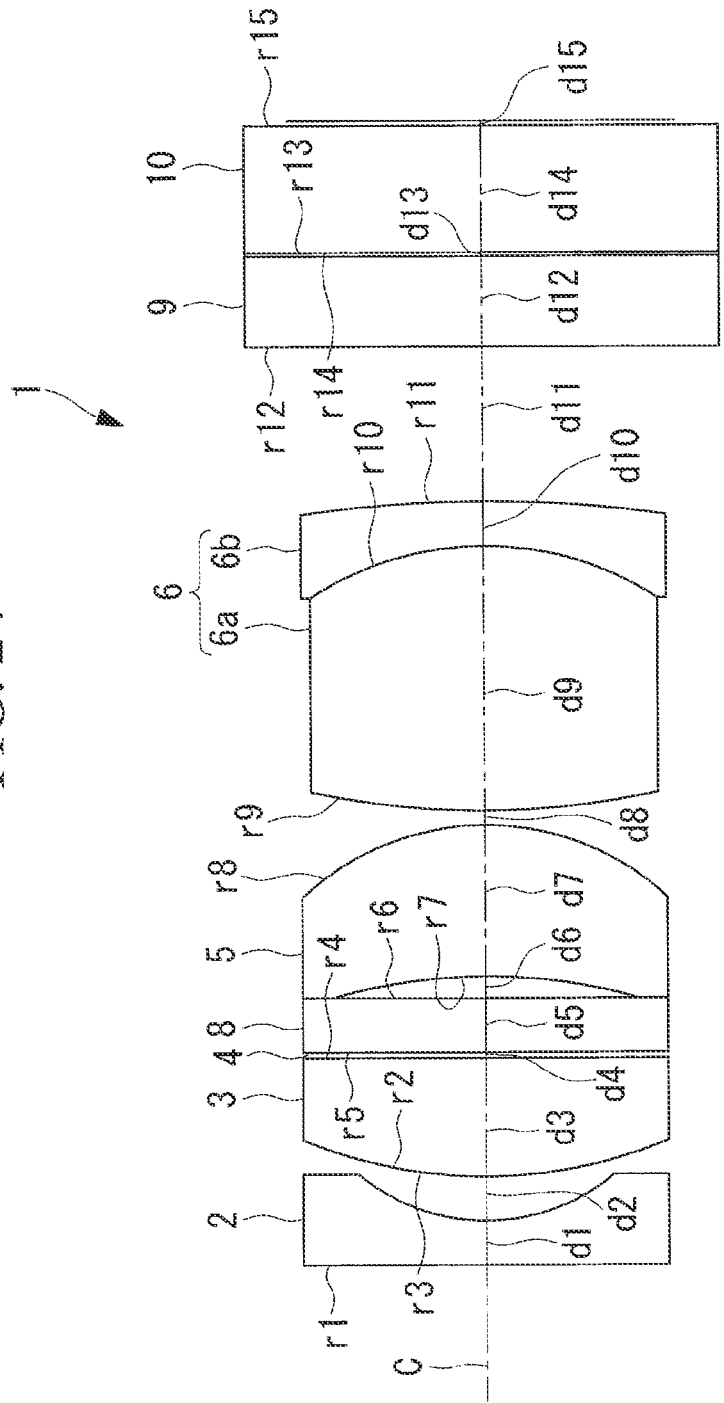
FIG. 24 is an illustration showing the lens arrangement of a twelfth example of the endoscope objective optical system in FIG. 1.
Figure 25:
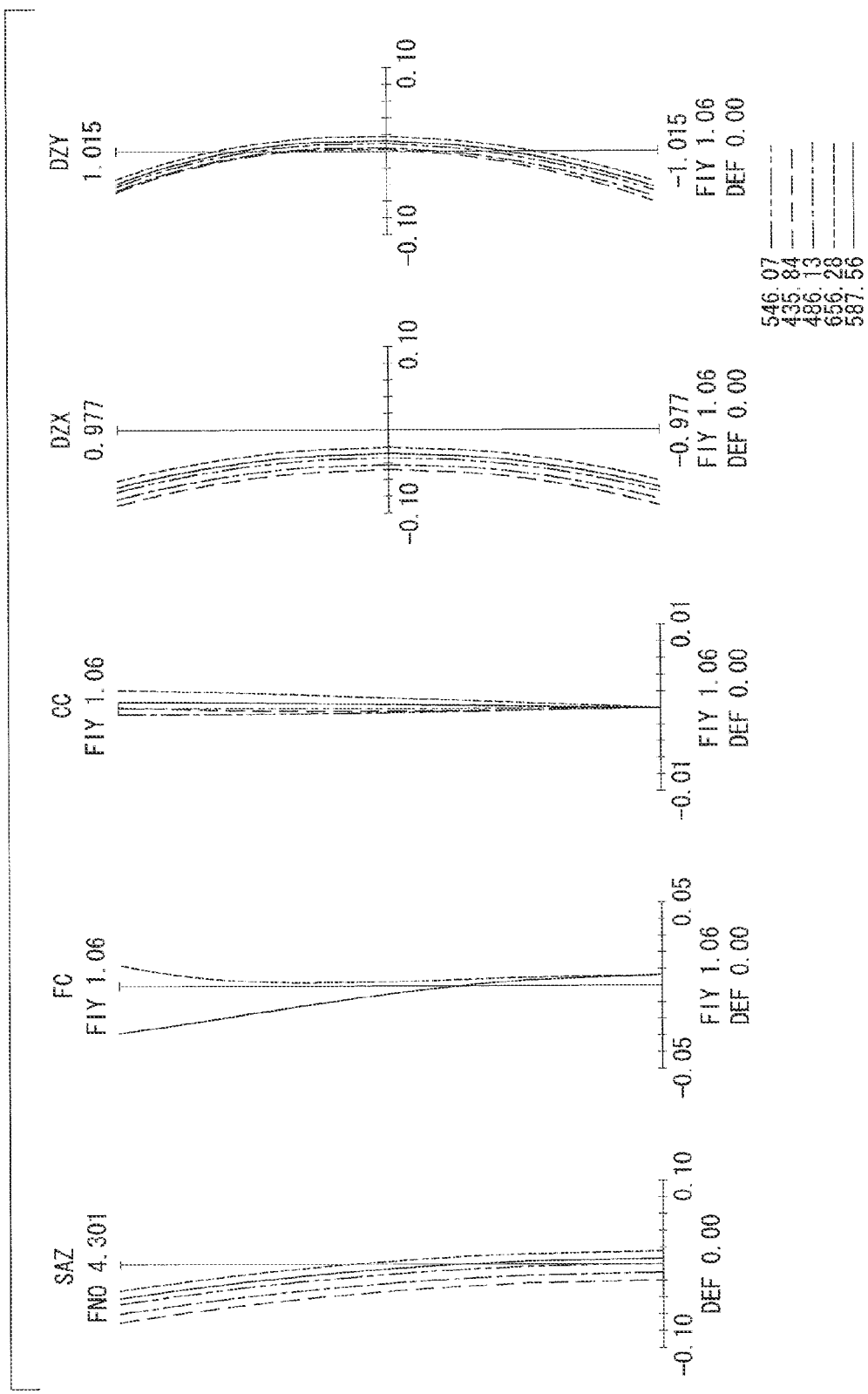
FIG. 25 is a set of aberration diagrams of the endoscope objective optical system having the lens arrangement in FIG. 24.

FIG. 24 shows the lens arrangement of the twelfth example of the endoscope objective optical system 1. Table 12 shows lens data. FIG. 25 shows a set of aberration diagrams.

TABLE 12

| SURFACE NUMBER | r | d | n | vd |
|---|---|---|---|---|
| OBJECT SURFACE | ∞ | 33.1000 | 1. | |
| 1 | ∞ | 0.2423 | 1.67790 | 55.34 |
| 2 | 1.0785 | 0.2441 | 1. | |
| 3 | 2.5550 | 0.6571 | 1.88300 | 40.76 |
| 4 | ∞ | 0.0300 | 1. | |
| 5 (APERTURE STOP) | ∞ | 0.3000 | 1.52134 | 74.98 |
| 6 | ∞ | 0.1200 | 1. | |
| 7 | −2.9744 | 0.8365 | 1.88300 | 40.76 |
| 8 | −1.4487 | 0.0800 | 1. | |
| 9 | 4.3909 | 1.4599 | 1.72916 | 54.68 |
| 10 | −1.7213 | 0.2457 | 1.92286 | 18.90 |
| 11 | −6.9271 | 0.8544 | 1. | |
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0262 | 1. | |
| IMAGE SURFACE | ∞ | 0. | | |

Thirteenth Example

Next, a thirteenth example of the endoscope objective optical system 1 according to this embodiment will be described.

Figure 26:
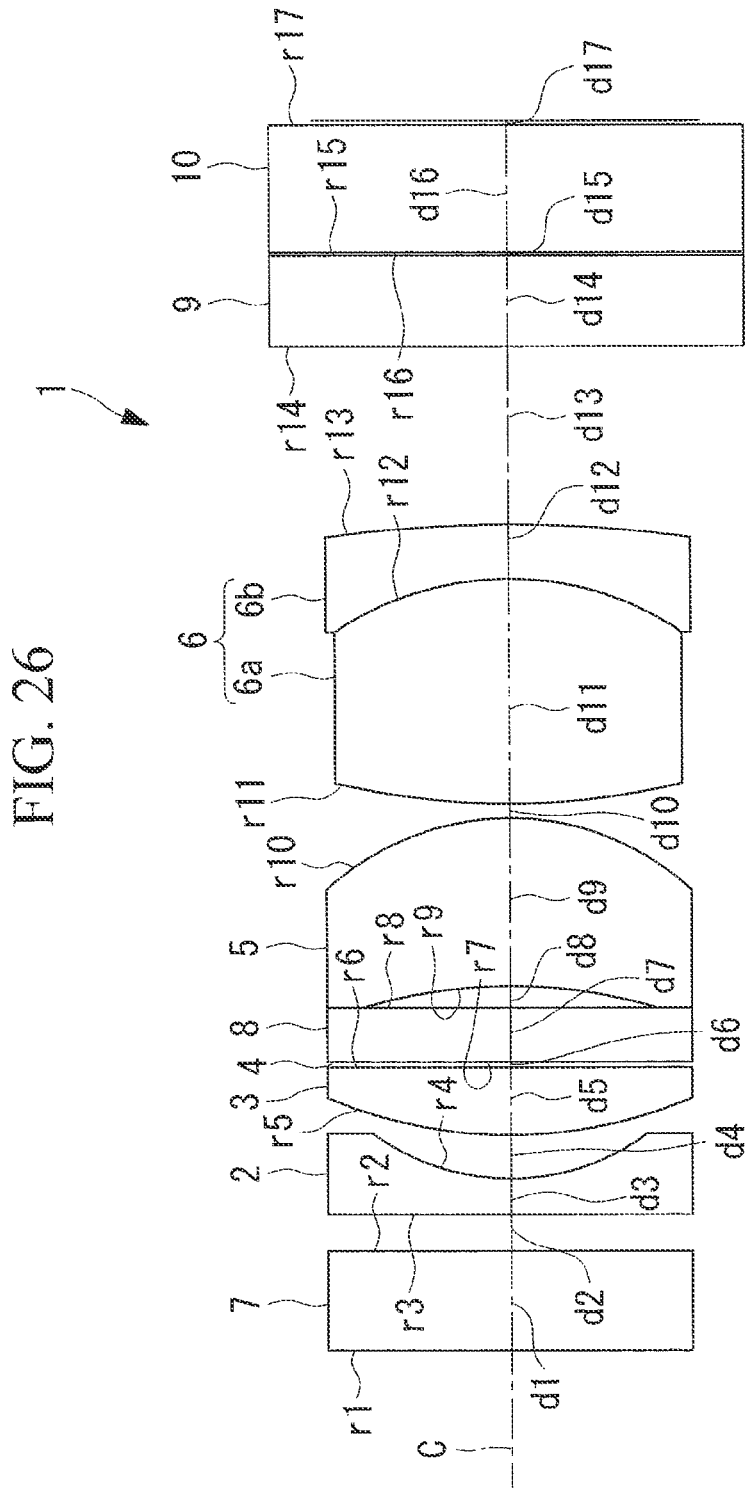
FIG. 26 is an illustration showing the lens arrangement of a thirteenth example of the endoscope objective optical system in FIG. 1.
Figure 27:
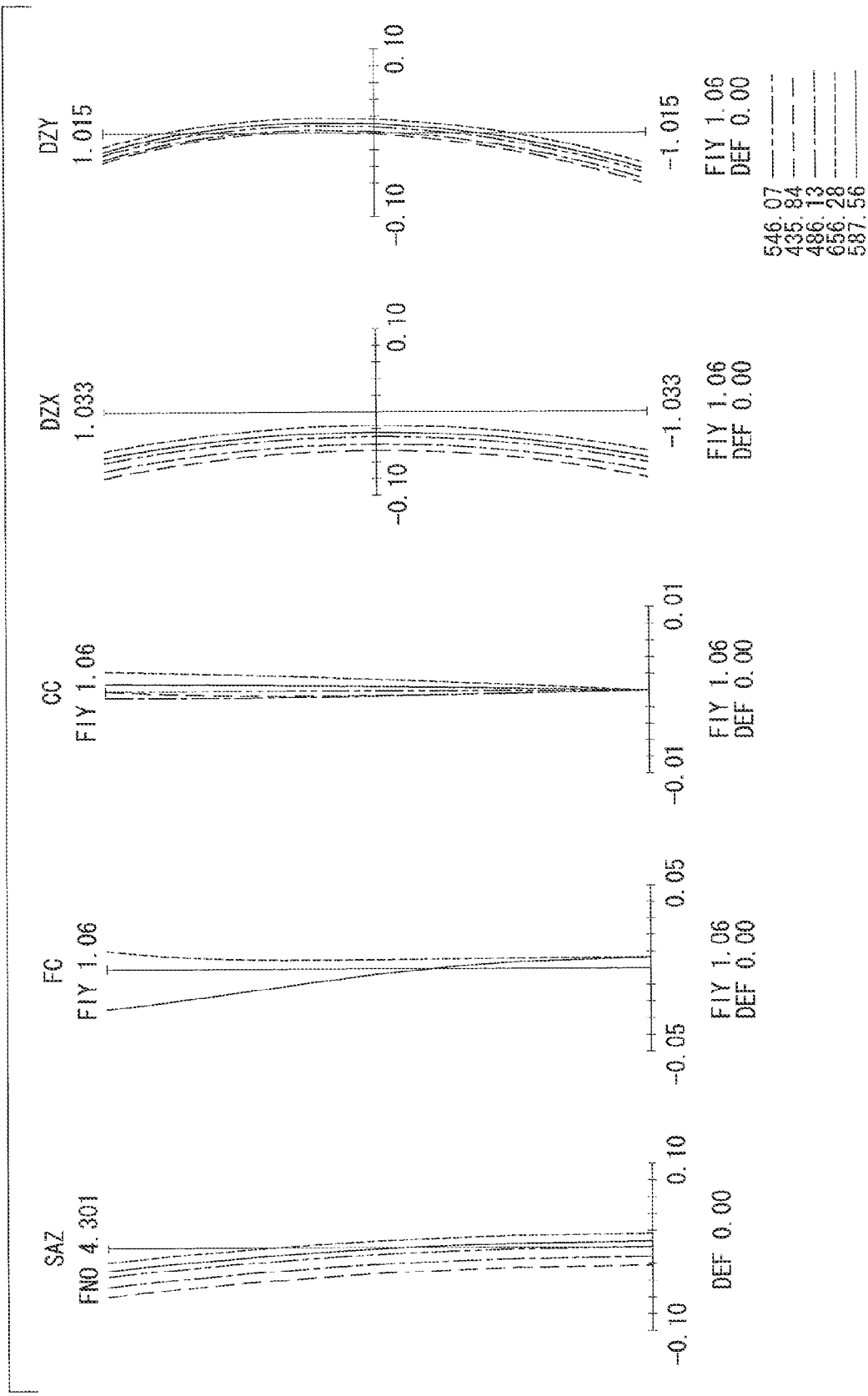
FIG. 27 is a set of aberration diagrams of the endoscope objective optical system having the lens arrangement in FIG. 26.

FIG. 26 shows the lens arrangement of the thirteenth example of the endoscope objective optical system 1. Table 13 shows lens data. FIG. 27 shows a set of aberration diagrams.

TABLE 13

| SURFACE NUMBER | r | d | n | vd |
|---|---|---|---|---|
| OBJECT SURFACE | ∞ | 33.1000 | 1. | |
| 1 | ∞ | 0.5500 | 1.76820 | 71.79 |
| 2 | ∞ | 0.2000 | 1. | |
| 3 | ∞ | 0.2468 | 1.58913 | 61.14 |
| 4 | 0.9879 | 0.1829 | 1. | |
| 5 | 2.5875 | 0.3769 | 1.88300 | 40.76 |
| 6 | ∞ | 0.0300 | 1. | |
| 7 (APERTURE STOP) | ∞ | 0.3000 | 1.52134 | 74.98 |
| 8 | ∞ | 0.1200 | 1. | |
| 9 | −2.7902 | 0.8986 | 1.88300 | 40.76 |
| 10 | −1.4030 | 0.0800 | 1. | |
| 11 | 4.3015 | 1.3872 | 1.72916 | 54.68 |
| 12 | −1.7179 | 0.2112 | 1.92286 | 18.90 |
| 13 | −6.7341 | 0.8115 | 1. | |
| 14 | ∞ | 0.5000 | 1.51633 | 64.14 |
| 15 | ∞ | 0.0200 | 1.51000 | 64.05 |
| 16 | ∞ | 0.7000 | 1.61062 | 50.49 |
| 17 | ∞ | 0.0250 | 1. | |
| IMAGE SURFACE | ∞ | 0. | | |

Fourteenth Example

Next, a fourteenth example of the endoscope objective optical system 1 according to this embodiment will be described.

Figure 28:
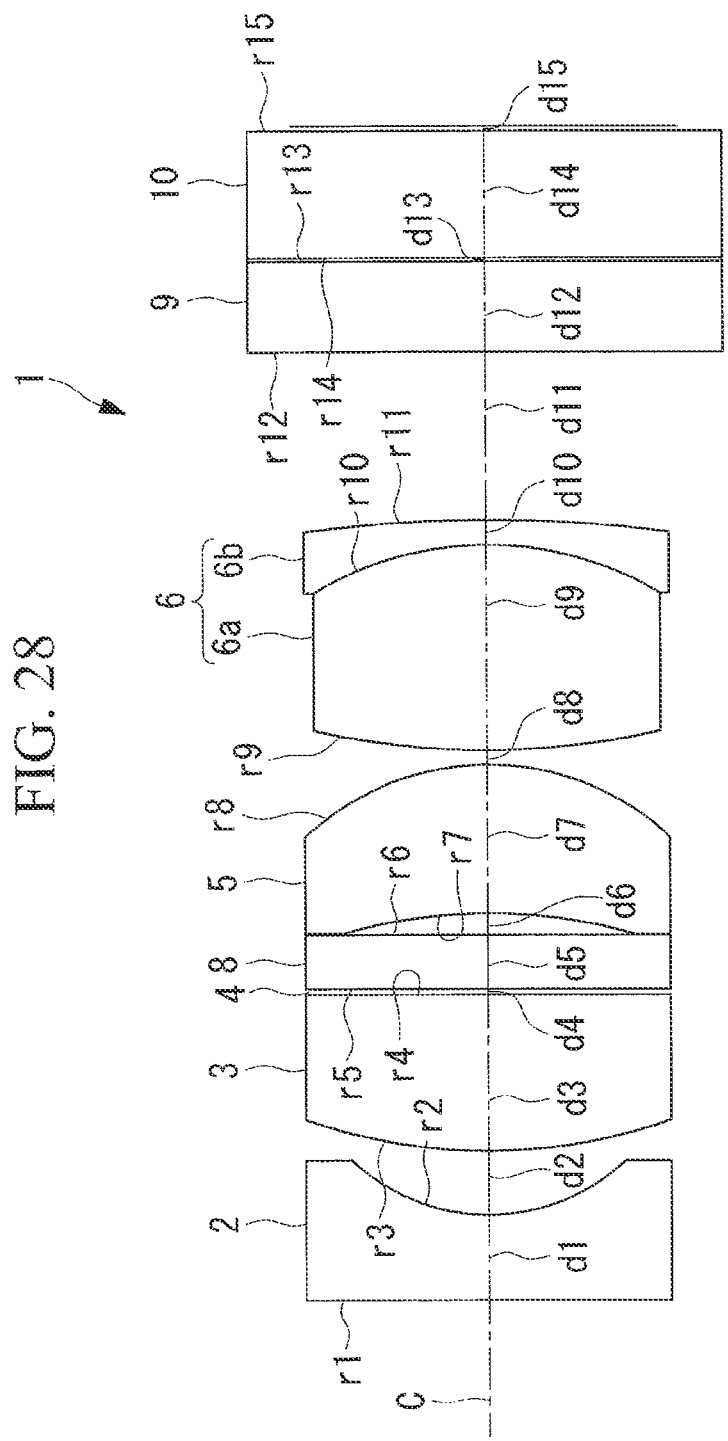
FIG. 28 is an illustration showing the lens arrangement of a fourteenth example of the endoscope objective optical system in FIG. 1.
Figure 29:
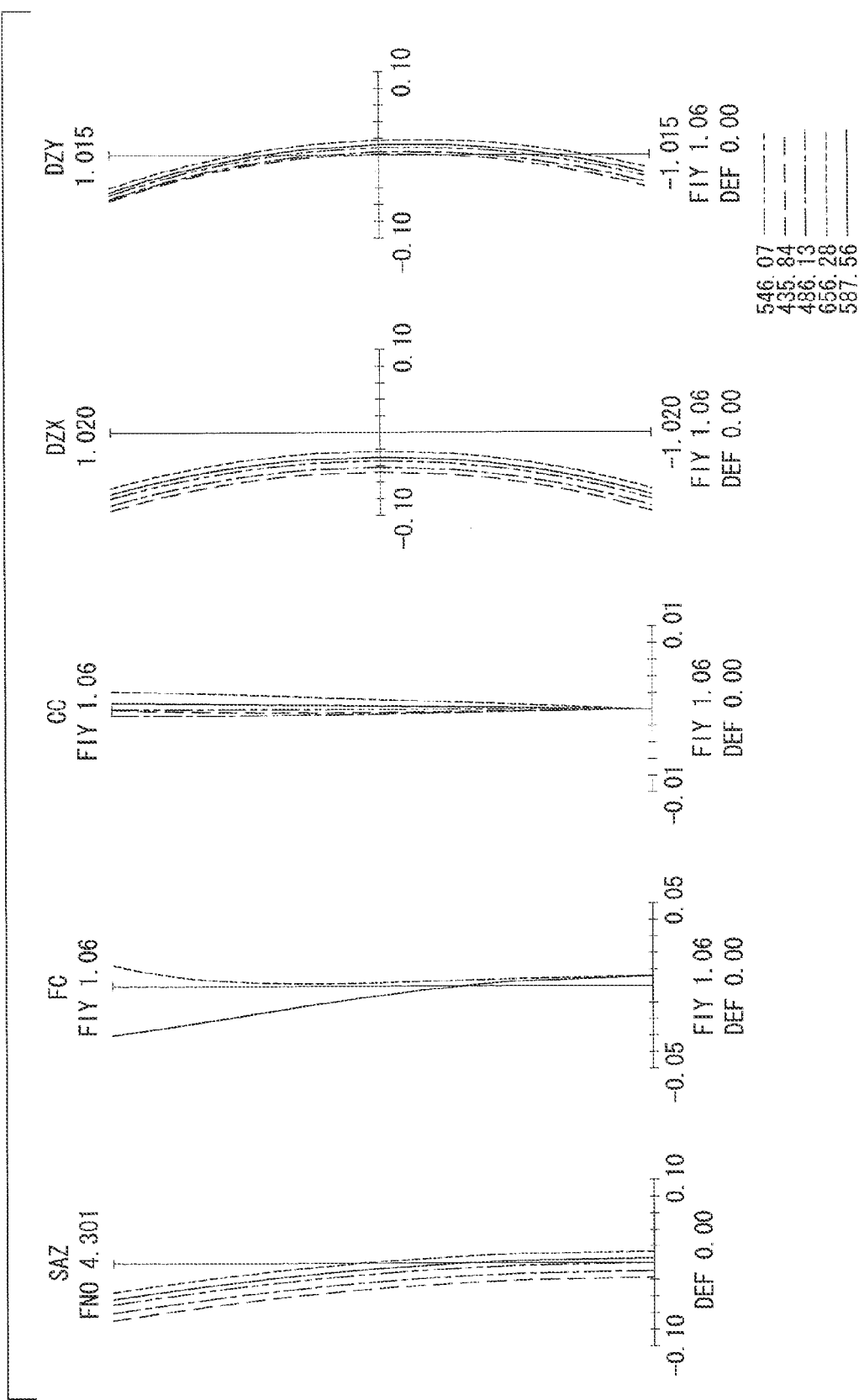
FIG. 29 is a set of aberration diagrams of the endoscope objective optical system having the lens arrangement in FIG. 28.

FIG. 28 shows the lens arrangement of the fourteenth example of the endoscope objective optical system 1. Table 14 shows lens data. FIG. 29 shows a set of aberration diagrams.

TABLE 14

| SURFACE NUMBER | r | d | n | vd |
|---|---|---|---|---|
| OBJECT SURFACE | ∞ | 33.1000 | 1. | |
| 1 | ∞ | 0.4716 | 1.58913 | 61.14 |
| 2 | 1.0848 | 0.3523 | 1. | |
| 3 | 2.9462 | 0.8656 | 1.88300 | 40.76 |
| 4 | ∞ | 0.0300 | 1. | |
| 5 (APERTURE STOP) | ∞ | 0.3000 | 1.52134 | 74.98 |
| 6 | ∞ | 0.1200 | 1. | |
| 7 | −2.9126 | 0.8219 | 1.88300 | 40.76 |
| 8 | −1.4521 | 0.0800 | 1. | |
| 9 | 4.2355 | 1.1306 | 1.72916 | 54.68 |
| 10 | −1.8395 | 0.1381 | 1.92286 | 18.90 |
| 11 | −7.6866 | 0.9273 | 1. | |
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0262 | 1. | |
| IMAGE SURFACE | ∞ | 0. | | |

Fifteenth Example

Next, a fifteenth example of the endoscope objective optical system 1 according to this embodiment will be described.

Figure 30:
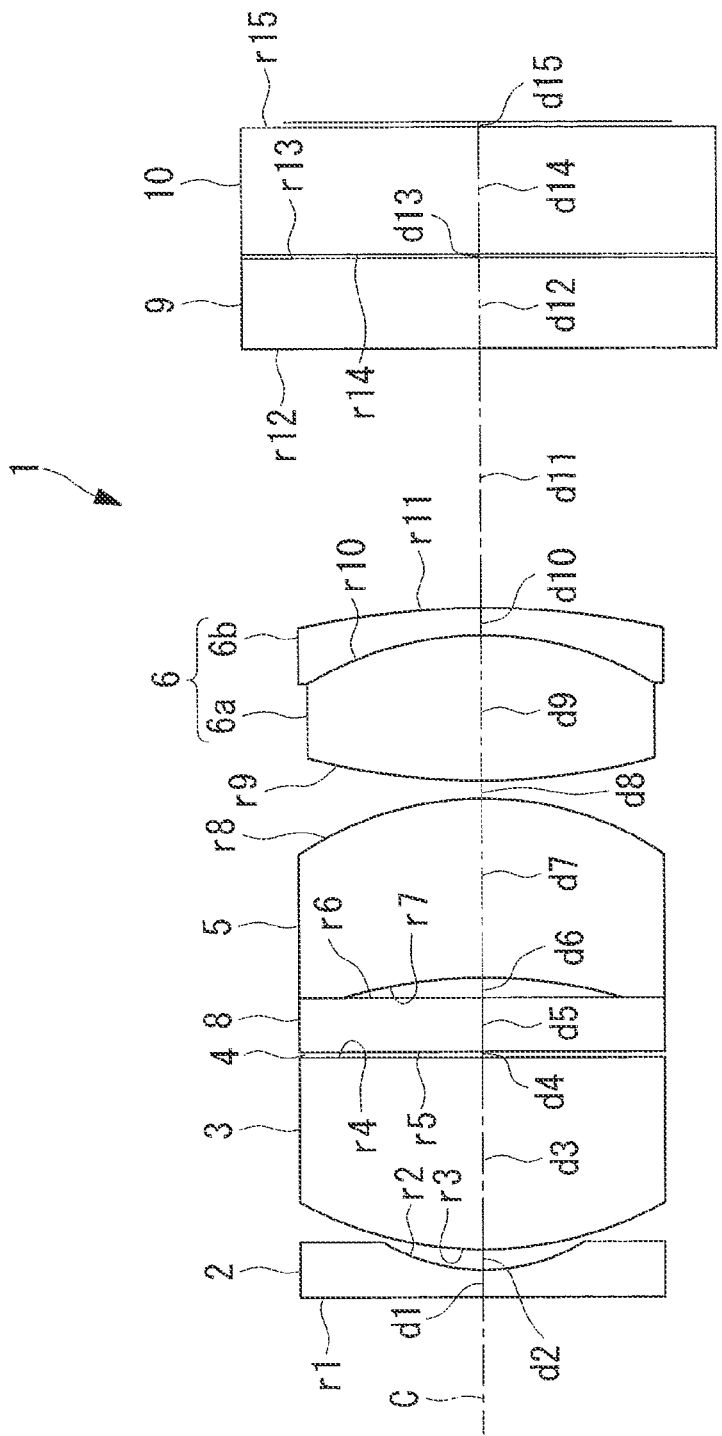
FIG. 30 is an illustration showing the lens arrangement of a fifteenth example of the endoscope objective optical system in FIG. 1.
Figure 31:
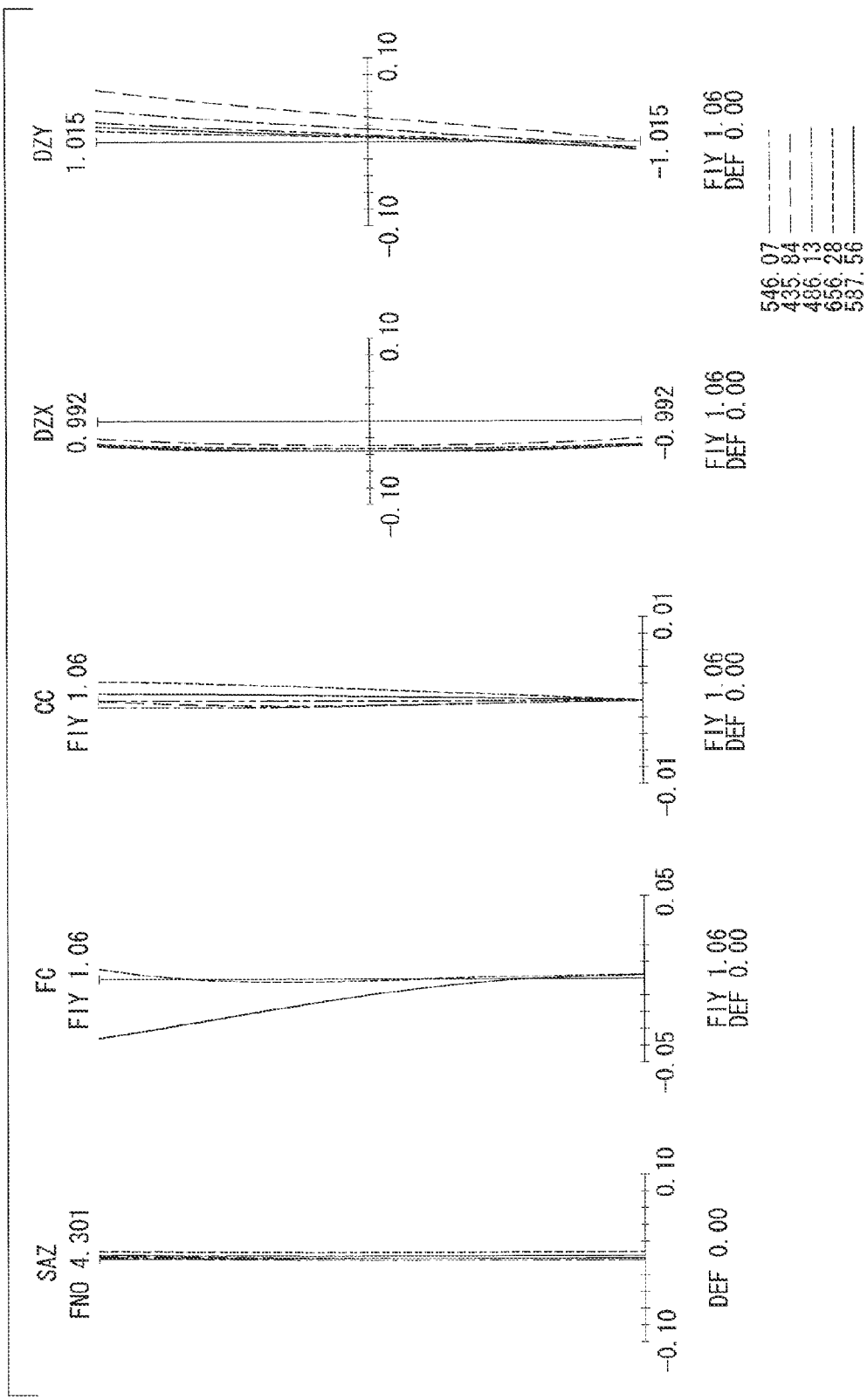
FIG. 31 is a set of aberration diagrams of the endoscope objective optical system having the lens arrangement in FIG. 30.

FIG. 30 shows the lens arrangement of the fifteenth example of the endoscope objective optical system 1. Table 15 shows lens data. FIG. 31 shows a set of aberration diagrams.

TABLE 15

| SURFACE NUMBER | r | d | n | vd |
|---|---|---|---|---|
| OBJECT SURFACE | ∞ | 33.1000 | 1. | |
| 1 | ∞ | 0.1495 | 1.69700 | 48.52 |
| 2 | 1.0562 | 0.1133 | 1. | |
| 3 | 2.0536 | 1.0627 | 1.88300 | 40.76 |
| 4 | ∞ | 0.0300 | 1. | |
| 5 (APERTURE STOP) | ∞ | 0.3000 | 1.52134 | 74.98 |
| 6 | ∞ | 0.1100 | 1. | |
| 7 | −2.7391 | 0.9909 | 1.88300 | 40.76 |
| 8 | −1.7748 | 0.1000 | 1. | |
| 9 | 3.6884 | 0.8000 | 1.72916 | 54.68 |
| 10 | −1.8370 | 0.1500 | 1.92286 | 18.90 |
| 11 | −4.6767 | 1.4336 | 1. | |

TABLE 15-continued

| SURFACE NUMBER | r | d | n | vd |
|---|---|---|---|---|
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0262 | 1. | |
| IMAGE SURFACE | ∞ | 0. | | |

Sixteenth Example

Next, a sixteenth example of the endoscope objective optical system 1 according to this embodiment will be described.

Figure 32:
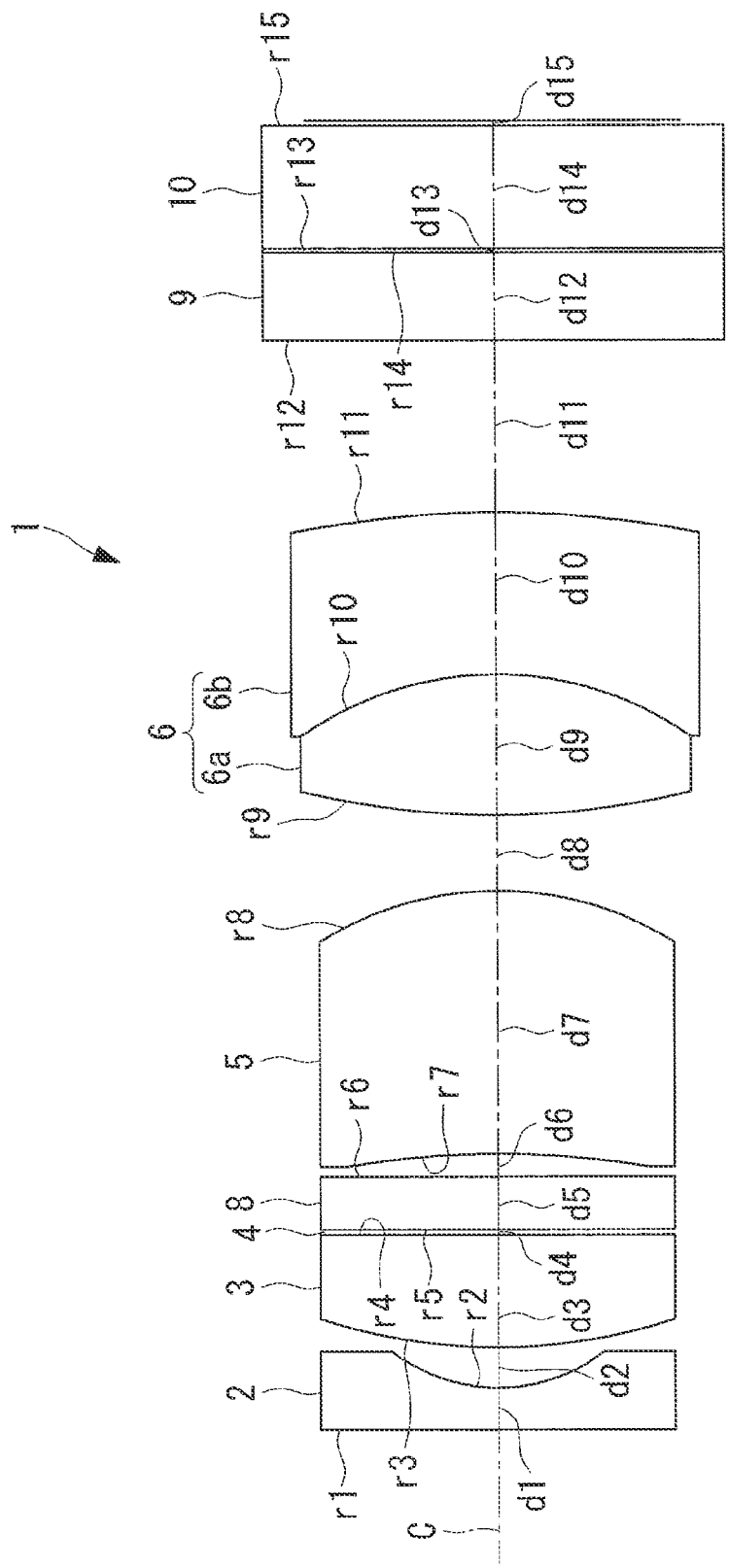
FIG. 32 is an illustration showing the lens arrangement of a sixteenth example of the endoscope objective optical system in FIG. 1.
Figure 33:
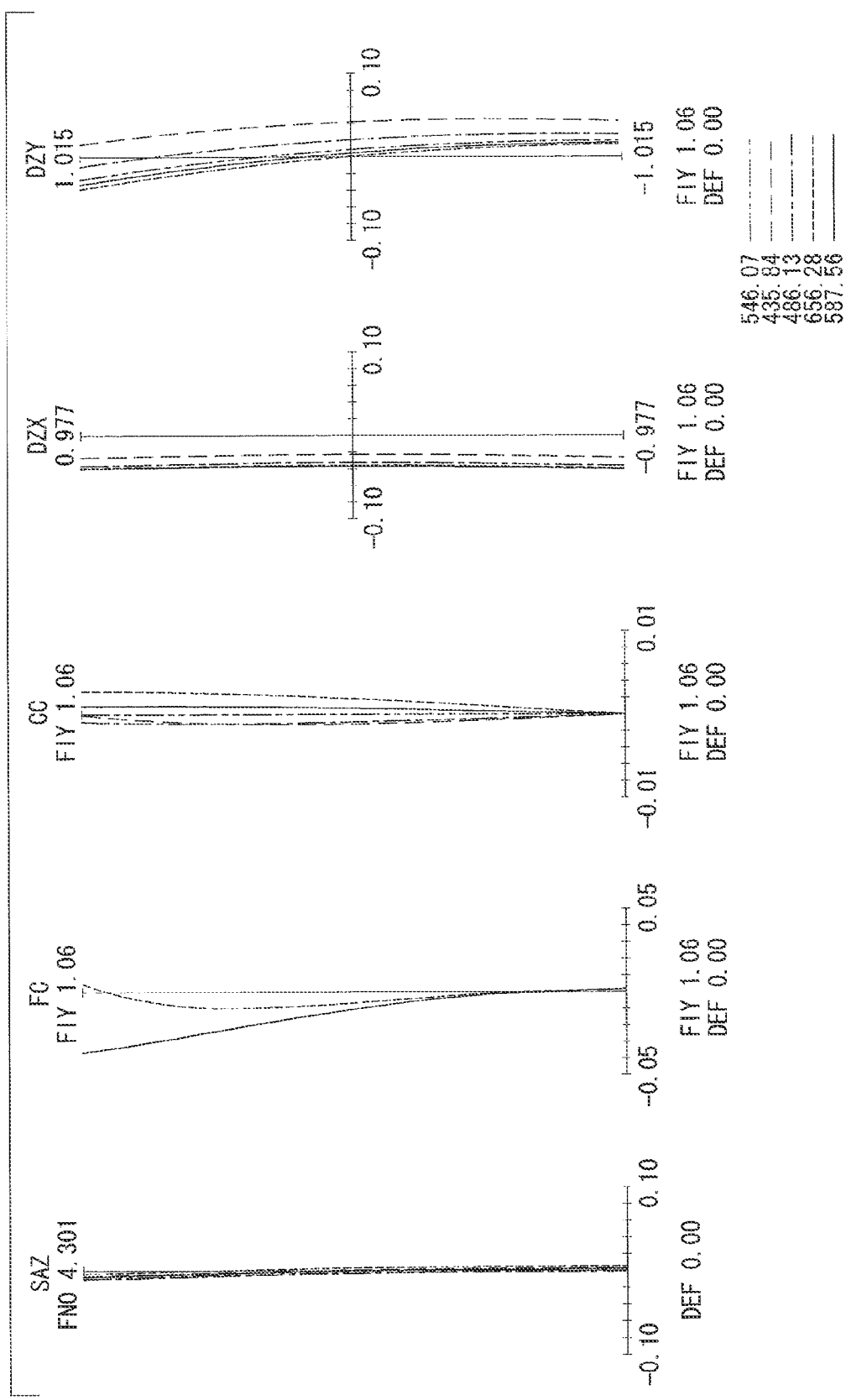
FIG. 33 is a set of aberration diagrams of the endoscope objective optical system having the lens arrangement in FIG. 32.

FIG. 32 shows the lens arrangement of the sixteenth example of the endoscope objective optical system 1. Table 16 shows lens data. FIG. 33 shows a set of aberration diagrams.

TABLE 16

| SURFACE NUMBER | r | d | n | vd |
|---|---|---|---|---|
| OBJECT SURFACE | ∞ | 33.1000 | 1. | |
| 1 | ∞ | 0.2383 | 1.51742 | 52.43 |
| 2 | 0.9780 | 0.2300 | 1. | |
| 3 | 3.2119 | 0.6388 | 1.88300 | 40.76 |
| 4 | ∞ | 0.0300 | 1. | |
| 5 (APERTURE STOP) | ∞ | 0.3000 | 1.52134 | 74.98 |
| 6 | ∞ | 0.1300 | 1. | |
| 7 | −4.9135 | 1.4972 | 1.88300 | 40.76 |
| 8 | −1.8622 | 0.4295 | 1. | |
| 9 | 4.5563 | 0.8000 | 1.72916 | 54.68 |
| 10 | −1.8919 | 0.9190 | 1.92286 | 18.90 |
| 11 | −5.7364 | 0.9776 | 1. | |
| 12 | ∞ | 0.5000 | 1.51633 | 64.14 |
| 13 | ∞ | 0.0200 | 1.51000 | 64.05 |
| 14 | ∞ | 0.7000 | 1.61062 | 50.49 |
| 15 | ∞ | 0.0263 | 1. | |
| IMAGE SURFACE | ∞ | 0. | | |

Seventeenth Example

Next, a seventeenth example of the endoscope objective optical system 1 according to this embodiment will be described.

Figure 34:
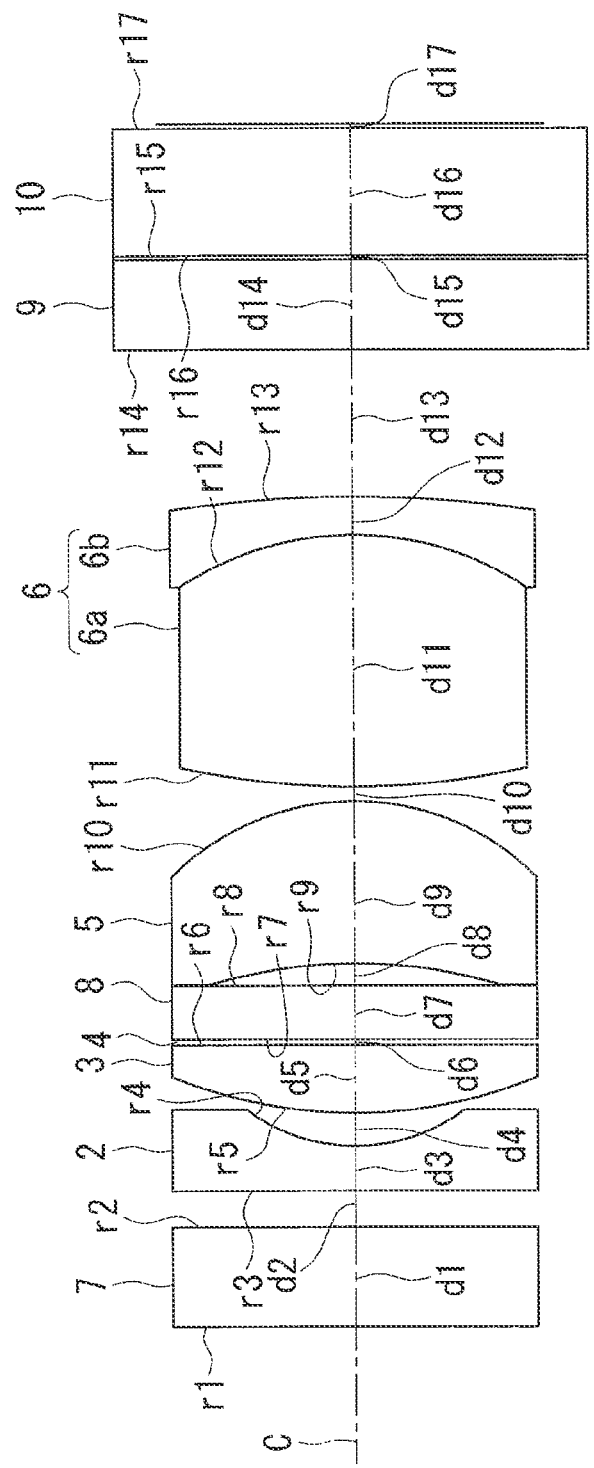
FIG. 34 is an illustration showing the lens arrangement of a seventeenth example of the endoscope objective optical system in FIG. 1.

FIG. 34 shows the lens arrangement of the seventeenth example of the endoscope objective optical system 1. Table 17 shows lens data. FIG. 35 shows a set of aberration diagrams.

TABLE 17

| SURFACE NUMBER | r | d | n | vd |
|---|---|---|---|---|
| OBJECT SURFACE | ∞ | 33.1000 | 1. | |
| 1 | ∞ | 0.5500 | 1.76820 | 71.79 |
| 2 | ∞ | 0.2000 | 1. | |
| 3 | ∞ | 0.1983 | 1.78590 | 44.20 |
| 4 | 1.2584 | 0.2397 | 1. | |
| 5 | 2.5201 | 0.3764 | 1.88300 | 40.76 |
| 6 | ∞ | 0.0300 | 1. | |
| 7 (APERTURE STOP) | ∞ | 0.3000 | 1.52134 | 74.98 |
| 8 | ∞ | 0.1200 | 1. | |
| 9 | −2.7371 | 0.9278 | 1.88300 | 40.76 |
| 10 | −1.4620 | 0.0800 | 1. | |
| 11 | 4.0291 | 1.2400 | 1.72916 | 54.68 |
| 12 | −1.6860 | 0.3000 | 1.92286 | 18.90 |
| 13 | −7.0976 | 0.9833 | 1. | |
| 14 | ∞ | 0.5000 | 1.51633 | 64.14 |
| 15 | ∞ | 0.0200 | 1.51000 | 64.05 |
| 16 | ∞ | 0.7000 | 1.61062 | 50.49 |

TABLE 17-continued

| SURFACE NUMBER | r | d | n | vd |
|---|---|---|---|---|
| 17 | ∞ | 0.0250 | 1. | |
| IMAGE SURFACE | ∞ | 0. | | |

All the values of conditions (1) to (6) in the first to seventeenth examples, as listed in Table 18, satisfy the respective conditions. In addition, the focal lengths, F-numbers, angles of view, and image heights in the first to seventeenth examples are as listed in Table 19.

TABLE 18

| NUMBER OF EXAMPLES | Df/f | n1 | n2−n1 | IH/f | f1/f | |r1|−|r2|+d1 |
|---|---|---|---|---|---|---|
| 1 | 0.864 | 1.517 | >0 | 0.697 | −1.240 | 2.212 |
| 2 | 1.100 | 1.697 | >0 | 0.692 | −0.910 | 2.083 |
| 3 | 1.138 | 1.697 | >0 | 0.646 | −0.922 | 10.512 |
| 4 | 1.014 | 1.678 | >0 | 0.696 | −1.004 | 2.452 |
| 5 | 1.139 | 1.678 | >0 | 0.692 | −0.936 | — |
| 6 | 0.300 | 1.517 | >0 | 0.696 | −1.256 | 2.396 |
| 7 | 0.632 | 1.729 | >0 | 0.696 | −0.837 | 2.203 |
| 8 | 1.106 | 1.786 | >0 | 0.696 | −0.749 | — |
| 9 | 0.782 | 1.786 | >0 | 0.688 | −0.759 | 2.203 |
| 10 | 1.108 | 1.517 | >0 | 0.696 | −1.082 | — |
| 11 | 1.000 | 1.623 | >0 | 0.635 | −0.958 | 8.282 |
| 12 | 0.712 | 1.678 | >0 | 0.657 | −0.986 | 2.362 |
| 13 | 0.500 | 1.589 | >0 | 0.655 | −1.035 | 2.286 |
| 14 | 1.122 | 1.589 | >0 | 0.702 | −1.219 | 2.282 |
| 15 | 0.800 | 1.697 | >0 | 0.637 | −0.910 | 1.955 |
| 16 | 0.668 | 1.517 | >0 | 0.634 | −1.135 | 4.549 |
| 17 | 0.500 | 1.786 | >0 | 0.648 | −0.978 | 2.203 |

TABLE 19

| NUMBER OF EXAMPLES | FOCAL LENGTHS | F-NUMBERS | ANGLES OF VIEW | IMAGE HIGHTS |
|---|---|---|---|---|
| 1 | 1.516 | 4.350 | 83.28 | 1.056 |
| 2 | 1.526 | 4.354 | 84.14 | 1.056 |
| 3 | 1.636 | 4.358 | 77.00 | 1.056 |
| 4 | 1.517 | 4.366 | 83.0. | 1.056 |
| 5 | 1.526 | 4.342 | 83.61 | 1.056 |
| 6 | 1.517 | 4.359 | 79.08 | 1.056 |
| 7 | 1.517 | 4.362 | 83.04 | 1.056 |
| 8 | 1.517 | 4.352 | 83.06 | 1.056 |
| 9 | 1.535 | 4.356 | 82.96 | 1.056 |
| 10 | 1.517 | 4.338 | 83.07 | 1.056 |
| 11 | 1.663 | 4.358 | 75.36 | 1.056 |
| 12 | 1.606 | 4.373 | 78.00 | 1.056 |
| 13 | 1.613 | 4.369 | 77.99 | 1.056 |
| 14 | 1.505 | 4.368 | 83.41 | 1.056 |
| 15 | 1.657 | 4.364 | 76.58 | 1.056 |
| 16 | 1.658 | 4.329 | 75.98 | 1.056 |
| 17 | 1.629 | 4.369 | 77.98 | 1.056 |

On the basis of the embodiment described above, inventions as follows are derived.

An aspect of the present invention provides an endoscope objective optical system including, in order from an object side, a first lens composed of a negative single lens, a second lens composed of a positive single lens, an aperture stop, a third lens composed of a positive single lens, and a fourth lens composed of a positive combined lens. The endoscope objective optical system satisfies the following conditions:

$$0.3 < Df/f < 1.15 \tag{1}$$

$$n1 < 1.79 \tag{2}$$

$$n2 > n1 \tag{3}$$

$$0.6 < IH/f < 0.83 \quad (4)$$

$$|r1| - |r2| + d1 > 1.8 \quad (5)$$

wherein Df is the distance from a surface of the first lens facing the object side to the aperture stop, f is the focal length of the entire system, n1 is the refractive index of the first lens (d-line), n2 is the refractive index of the second lens (d-line), IH is the maximum image height of the entire system, r1 is the radius of curvature of a surface of the third lens facing the object side, r2 is the radius of curvature of the surface of the third lens facing the image side, and d1 is the center thickness of the third lens.

According to the aspect of the present invention, the endoscope objective optical system has a relatively narrow angle and a short overall length and allows simultaneous correction for field curvature and comatic aberration.

Satisfying condition (1) decreases the ray height on the object side and thus allows for a small outer diameter. If Df/f is 0.3 or less, the first lens and the second lens are difficult to fabricate. If Df/f is 1.15 or more, the system has a large outer diameter and does not allow correction for field curvature while maintaining a narrow angle. Satisfying condition (2) allows correction for both field curvature and comatic aberration while maintaining a short overall length. Satisfying condition (3) allows correction for field curvature while maintaining a short overall length. Satisfying condition (4) allows the objective optical system to have a narrow angle. Satisfying condition (5) results in a long distance between the centers of curvature of both surfaces of the third lens. A long distance allows the centers of curvature to be accurately linked during a lens fabrication process, and therefore, the optical axis can be accurately determined. Thus, the third lens can be accurately fabricated.

In the aspect, the endoscope objective optical system preferably satisfies the following condition:

$$n1 < 1.70 \quad (2')$$

Another aspect of the present invention provides an endoscope objective optical system including, in order from an object side, a first lens composed of a negative single lens, a second lens composed of a positive single lens, an aperture stop, a third lens composed of a positive single lens, and a fourth lens composed of a positive combined lens, wherein the first lens has a flat surface facing the object side, the second lens has a flat surface facing an image side, and the third lens has a meniscus shape having a convex surface facing the image side. The endoscope objective optical system satisfies the following conditions:

$$0.3 < Df/f < 1.15 \quad (1)$$

$$n1 < 1.79 \quad (2)$$

$$n2 > n1 \quad (3)$$

$$0.6 < IH/f < 0.83 \quad (4)$$

wherein Df is the distance from a surface of the first lens facing the object side to the aperture stop, f is the focal length of the entire system, n1 is the refractive index of the first lens (d-line), n2 is the refractive index of the second lens (d-line), IH is the maximum image height of the entire system.

This aspect facilitates fabrication, thus contributing to cost reduction. In addition, because the lenses and the frames are received by flat surfaces, the lenses can be fixed to the frames without being off-center.

The invention claimed is:

1. An endoscope objective optical system comprising, in order from an object side, a first lens comprising a negative single lens, a second lens comprising a positive single lens, an aperture stop, a third lens comprising a positive single lens, and a fourth lens comprising a positive combined lens, wherein the first lens has a flat surface facing the object side, the second lens has a flat surface facing an image side, and the third lens has a meniscus shape having a convex surface facing the image side, the endoscope objective optical system satisfying the following conditions:

$$0.3 < Df/f < 1.15 \quad (1)$$

$$n1 < 1.79 \quad (2)$$

$$n2 > n1 \quad (3)$$

$$0.6 < IH/f < 0.83 \quad (4)$$

wherein
- Df is the distance from a surface of the first lens facing the object side to the aperture stop,
- f is the focal length of the entire system,
- n1 is the refractive index of the first lens (d-line),
- n2 is the refractive index of the second lens (d-line),
- IH is the maximum image height of the entire system.

2. The endoscope objective optical system according to claim 1, wherein the endoscope objective optical system satisfies the following condition:

$$n1 < 1.70. \quad (2')$$

* * * * *